United States Patent [19]
Moll et al.

[11] Patent Number: 5,514,075
[45] Date of Patent: May 7, 1996

[54] PROPERITONEAL MECHANICAL RETRACTION APPARATUS AND METHODS OF USING

[75] Inventors: Frederic H. Moll, San Francisco; Albert K. Chin, Palo Alto; Rick J. Kaufmann, Los Gatos; Charles Gresl, Jr., San Francisco, all of Calif.

[73] Assignee: Origin Medsystems, Inc., Menlo Park, Calif.

[21] Appl. No.: 341,708

[22] Filed: Nov. 18, 1994

Related U.S. Application Data

[63] Continuation of Ser. No. 253,184, Jun. 2, 1994, abandoned, which is a continuation of Ser. No. 890,033, May 28, 1992, abandoned, which is a continuation-in-part of Ser. No. 706,781, May 29, 1991, abandoned.

[51] Int. Cl.⁶ .................................................. A61B 17/02
[52] U.S. Cl. ..................... 600/202; 600/204; 600/210; 600/215; 606/198
[58] Field of Search .................. 128/20, 17; 606/198, 606/205–208; 600/204, 210, 215, 218, 219, 225, 235, 202, 216

[56] References Cited

U.S. PATENT DOCUMENTS

| | | | |
|---|---|---|---|
| 1,798,124 | 3/1931 | Hunn. | |
| 2,841,148 | 7/1958 | Kadavy | 128/303 |
| 3,039,468 | 6/1962 | Price | 128/347 |
| 4,052,980 | 10/1977 | Grams et al. | 128/18 |
| 4,165,746 | 8/1979 | Burgin | 606/208 |
| 4,622,955 | 11/1986 | Fakhrai | 128/20 |
| 4,709,040 | 11/1987 | Mueller et al. | 128/334 R |
| 5,152,279 | 10/1992 | Wilk | 128/17 |
| 5,178,133 | 1/1993 | Pena | 128/20 |
| 5,235,966 | 8/1993 | Jamner | 128/20 |
| 5,271,385 | 12/1993 | Bailey | 128/20 |
| 5,279,575 | 1/1994 | Sugarbaker | 604/174 |
| 5,280,782 | 1/1994 | Wilk | 128/20 |
| 5,289,817 | 3/1994 | Williams et al. | 128/20 |
| 5,293,863 | 3/1994 | Zhu et al. | 128/20 |
| 5,318,012 | 6/1994 | Wilk | 128/20 |
| 5,318,013 | 6/1994 | Wilk | 128/20 |
| 5,339,801 | 8/1994 | Poloyko et al. | 128/20 |
| 5,351,679 | 10/1994 | Mayzels et al. | 128/20 |

FOREIGN PATENT DOCUMENTS

| | | |
|---|---|---|
| 464463A | 1/1992 | European Pat. Off.. |
| 9104383 | 7/1991 | Germany. |
| 9102493 | 3/1991 | WIPO. |
| 9114392 | 10/1991 | WIPO. |

OTHER PUBLICATIONS

M. M. Gazayerli, "The Gazayerli Endoscopic Retractor, Model 1;" Surgical Laparoscopy & Endoscopy, vol. 1, No. 2, pp. 98–100 Raven Press, New York, Jun. 1991.

*Primary Examiner*—Michael H. Thaler
*Attorney, Agent, or Firm*—Limbach & Limbach

[57] ABSTRACT

A fan retractor has a pair of angle-shaped elements moveable relative to one another. The angle-shaped elements include first legs disposed in a generally parallel relationship, and second legs that extend laterally from the first legs, and are adapted for engaging with the abdominal wall. The second legs fan out upon rotation of the first legs relative to one another and have an effective thickness, measured in the direction defined by the first legs, that decreases distally from the first legs. The retractor also includes a lifting device that applies a lifting force to the angle-shaped elements.

In variations, the second legs have a stiffness that decreases distally from the first legs; the first legs are linked so as to contrarotate relative to one another; the retractor includes a lifting force indicator; and the lifting device unidirectionally applies the lifting force to the angle-shaped elements.

The fan retractor is preferably used properitoneally, that is, the second legs of the retractor are inserted between the properitoneal fat layer and the peritoneum. With this placement of the retractor, the peritoneum provides a drape over the bowel and omentum and prevents the second legs of the retractor from snagging the bowel or the omentum. The fan retractor may additionally be used conventionally with its second legs placed posteriorly relative to the peritoneum.

54 Claims, 9 Drawing Sheets

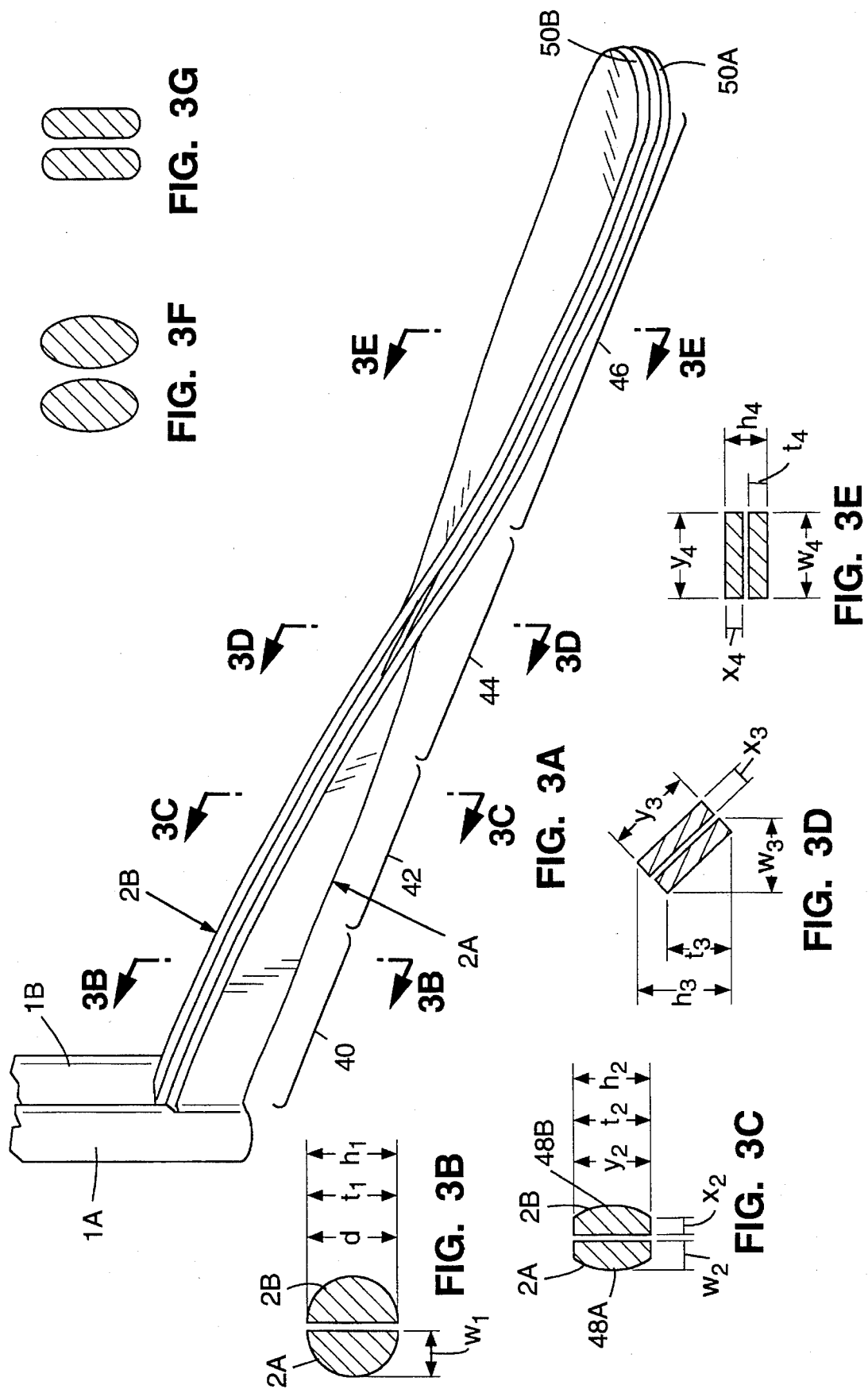

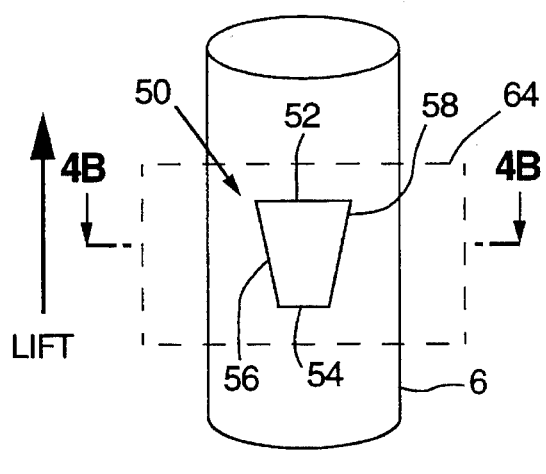
FIG. 4A
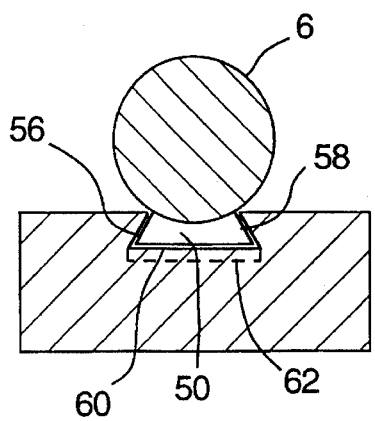
FIG. 4B
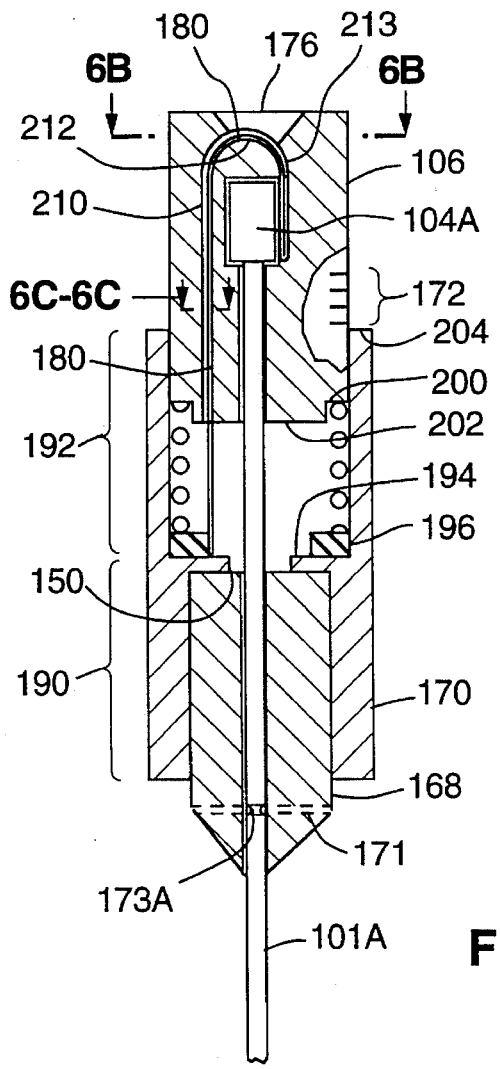
FIG. 6A
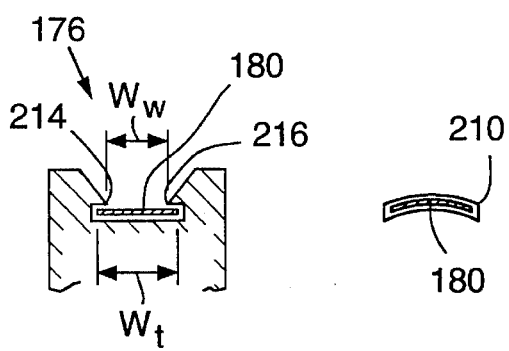
FIG. 6B    FIG. 6C

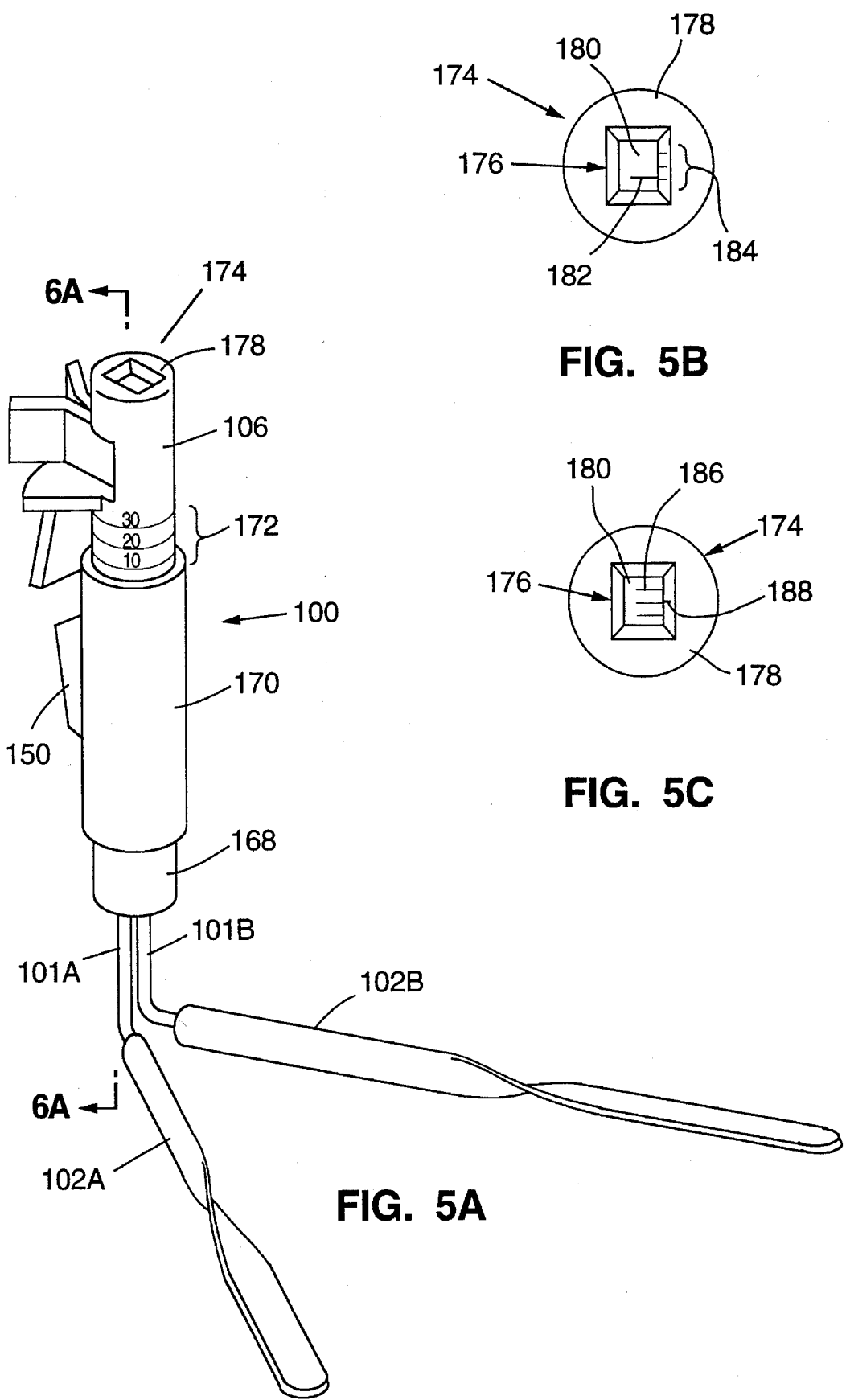

PROPERITONEAL MECHANICAL RETRACTION APPARATUS AND METHODS OF USING

This is a continuation of application Ser. No. 08/253,184 filed on Jun. 2, 1994 now abandoned; which is a continuation of Ser. No. 07/890,033; filed on May 28, 1992 now abandoned; which is a continuation-in-part of application Ser. No. 07/706,781 filed on May 29, 1991 now abandoned.

BACKGROUND OF THE INVENTION

Laparoscopy dates back to the turn of the 20th Century. Early laparoscopic techniques were used primarily for diagnostic purposes to view the internal organs, without the necessity of conventional surgery. Since the 1930s, laparoscopy has been used for sterilization and, more recently, for suturing hernias. U.S. Pat. Nos. 4,919,152 and 4,944,443 are concerned with techniques for suturing hernias. Another recent innovation is the use of laparoscopic surgery for removing the gallbladder.

In the course of performing laparoscopic procedures in the abdomen, it is necessary to raise the abdominal wall to create space in which to work. A well-known method of raising the abdominal wall is to insufflate the abdominal cavity with a suitable insufflation gas, such as air, or carbon dioxide. A significant disadvantage of gas insufflation is that instruments must be passed into the abdominal cavity through gas-tight seals, which significantly reduce the surgeon's feel of the instruments.

Several mechanical alternatives to gas insufflation have been proposed. The Gazayerli Endoscopic Retractor Model 1, described in SURGICAL LAPAROSCOPY AND ENDOSCOPY, Vol. 1, No. 2, 1991, pages 98–100, has a rigid rod with a hinged blade at the distal end. The blade can rotate through 360 degrees about an axis perpendicular to the long axis of the rod. The blade is aligned with the long axis of the rod for insertion into the abdomen through a small puncture. Once inside the abdomen, the blade is swivelled through about 90 degrees to form a T-shaped structure. The proximal end of the rod can be raised by hand or by a rope, pulley and weight arrangement. Raising the rod causes the blade to engage the abdominal wall and to lift it.

French patent application no. 90-03980 shows a wire structure that is threaded into the belly through a small puncture to engage and to lift the abdominal wall. The application also shows a fan retractor that has a first angle-shaped member having a first leg that engages with the abdominal wall, a tubular second leg having a bore, and a third leg, remote from the first leg, that has a hook-shaped member on its end distal from the second leg. A second angle-shaped member has a first leg that engages with the abdominal wall, a second leg that pivots within the bore of the second leg of the first angle-shaped member, and a third leg, remote from the first leg, that serves as an operating lever for the second angle-shaped member. The first legs of the angle-shaped members are closed together to insert them into the abdominal cavity through an incision. The third leg of the second angle-shaped member is then operated to spread the first leg of the second angle-shaped member apart from the first leg of the first angle-shaped member. The first legs are engaged with the peritoneum inside the abdominal cavity. A lifting force is then applied to the hookshaped member to lift the retractor and hence to lift the abdominal wall.

U.S. patent application Ser. No. 706,781, the application of which this application is a Continuation-in-Part, describes a number of different mechanical devices that are inserted through one or more punctures into the belly. All or part of the device is then lifted to lift the abdominal wall away from the underlying abdominal organs. One of the devices described in the prior application is a fan retractor that is inserted in a closed condition into the abdominal cavity, spread apart once inside the abdominal cavity, and brought into contact with the peritoneum inside the abdominal cavity. The apparatus is then lifted to lift the abdominal wall.

The known fan retractors are all intended for intra-abdominal placement. It is difficult to place the peritoneum-engaging elements of such devices inside the abdominal cavity adjacent to the peritoneum without snagging the bowel or omentum. It is often necessary to make multiple attempts at inserting the retractor before the fan retractor can be correctly positioned with its peritoneum-engaging elements adjacent to the peritoneum with no bowel or omentum caught between the peritoneum-engaging elements and the peritoneum. Insufflating the abdomen before inserting the fan retractor does not eliminate the risk of snagging.

If the retractor is inserted, lifted, and maintained in a lifted state with an unrecognized loop of bowel caught between the peritoneum-engaging elements of the retractor and the peritoneum, trauma or necrosis to that loop of bowel may occur, with significant morbidity or mortality.

Known fan retractors have a substantially constant stiffness along the length of their peritoneum-engaging elements. This causes the pressure that the peritoneum-engaging elements exert against the peritoneum to increase sharply towards the ends of the peritoneum-engaging elements. High pressure can cause trauma to the peritoneum, and there is a risk that the ends of the peritoneumengaging elements will penetrate the peritoneum.

The peritoneum-engaging elements of known fan retractors move independently of one another. This can lead to the peritoneum-engaging elements of the fan retractor being asymmetrically placed within the abdominal cavity, which results in the peritoneum-engaging elements providing the retracting force unequally. With asymmetrical placement, there is the risk that the more heavily loaded peritoneum engaging element will traumatize or penetrate the peritoneum.

The lifting force applied by known fan retractors is generally determined by the lifting result obtained. If, for some reason, the abdominal wall fails to lift, the lifting force could accidentally be increased to the point at which trauma to or penetration of the peritoneum occurs.

Known fan retractors are rigidly attached to lifting bars such that, if the lifting bar is carelessly lowered at the end of treatment, the lifting bar can push the fan retractor into the abdomen, and cause a compression injury to the underlying organs.

SUMMARY OF THE INVENTION

In the following description, the word "organ" will be used to mean an organ or a tissue that is retracted by a retraction device. The word "treat" will be used to mean both treat and observe, and the word "treatment" will be used to mean both treatment and observation. The word "tissue" or the phrase "tissue to be treated" will both be used to mean the organ or the tissue that is treated through or inside a retraction device.

A fan retractor according to the first aspect of the invention has a pair of angle-shaped elements moveable relative to one another. The angle-shaped elements include first legs disposed in a generally parallel relationship, and second legs that extend laterally from the first legs, and are adapted to engage with the abdominal wall. The second legs fan out upon rotation of the first legs relative to one another and have an effective thickness, measured in the direction defined by the first legs, that decreases distally from the first legs. The retractor also includes a lifting device that applies a lifting force to the angle-shaped elements.

The fan retractor according to the first aspect of the invention is used properitoneally, that is, the second legs of the retractor are inserted between the peritoneal fat layer and the peritoneum. With this placement of the retractor, the peritoneum provides a drape over the bowel and omentum and prevents the second legs of the retractor from snagging the bowel or the omentum.

The second legs have a thickness that decreases distally from the first legs. This enables the second legs act as a wedge to separate the peritoneum from the properitoneal fat layer, and provides a stiffness that decreases distally from the second legs. This enables the second legs to flex slightly, and to conform to the curvature of the abdominal wall. The second legs conforming to the curvature of the abdominal wall enables the second legs to exert a lifting force to the abdominal wall that is substantially constant along the length of the second legs. This reduces the risk of the distal ends of the second legs traumatizing or penetrating the abdominal wall.

A fan retractor according to a second aspect of the invention has a pair of angle-shaped elements moveable relative to one another. The angle-shaped elements include first legs disposed in a generally parallel relationship, and second legs that extend laterally from the first legs, and are adapted to engage with the abdominal wall. The second legs fan out upon rotation of the first legs relative to one another and have a stiffness, measured in the direction defined by the first legs, that decreases distally from the first legs. The retractor also includes a lifting device that applies a lifting force to the angle-shaped elements.

The fan retractor according to the second aspect of the invention is preferably used properitoneally and confers the advantages of properitoneal use described above in connection with the fan retractor according to the first aspect of the invention. However, a fan retractor according to the second aspect of the invention may also be used conventionally, i.e., it may apply its lifting force to the posterior side of the peritoneum.

Whether used properitoneally or conventionally, the second legs have a stiffness that decreases distally from the first legs. This characteristic enables the second legs to flex slightly, and to conform to the curvature of the abdominal wall. The second legs conforming to the curvature of the abdominal wall enables the second legs to exert a lifting force to the abdominal wall that is substantially constant along the length of the second legs. This reduces the risk of the distal ends of the second legs traumatizing or penetrating the abdominal wall.

A fan retractor according to the third aspect of the invention has a pair of angle-shaped elements moveable relative to one another. The angle-shaped elements include first legs disposed in a generally parallel relationship, and second legs extending laterally from the first legs. The second legs fan out upon rotation of the first legs relative to one another, are adapted to engage with the abdominal wall. The retractor also include a contrarotating device that responds to rotation of the first leg of one of the angle-shaped elements through a first angle. The contrarotating device rotates the first leg of the other of the first angle-shaped elements through an angle substantially equal and opposite to the first angle. Finally, the retractor includes a lifting device that applies a lifting force to the angle-shaped elements.

The contrarotating device makes the second legs fan out symmetrically. This feature is especially useful when the fan retractor is used properitoneally, since the position of the second legs cannot be directly seen when the second legs are between the peritoneal fat layer and the peritoneum. With symmetrical fanning, the risk that one of the second legs may inadvertently abut, and possibly pierce, the abdominal side wall is significantly reduced. A fan retractor according to the third aspect of the invention can also be used conventionally.

A fan retractor according to the fourth aspect of the invention has a pair of angle-shaped elements moveable relative to one another. The angle-shaped elements include first legs disposed in a generally parallel relationship, and second legs extending laterally from the first legs. The second legs fan out upon rotation of the first legs relative to one another, and are adapted to engage with the abdominal wall. The retractor also includes a lifting device that applies a lifting force to the angle-shaped elements. Finally, the retractor includes a lifting force measuring device that is coupled to the lifting device and that measures the lifting force.

A fan retractor according to the fourth aspect of the invention enables the lifting force to be monitored during the lifting operation. This prevents an excessive lifting force, that could possibly result in trauma to or penetration of the abdominal wall, from being applied to the abdominal wall. A fan retractor according to the fourth aspect of the invention is preferably used properitoneally, but it can also be used conventionally.

A fan retractor according to a fifth aspect of the invention has a pair of angle-shaped elements moveable relative to one another. The angle-shaped elements include first legs disposed in a generally parallel relationship, and second legs extending laterally from the first legs. The second legs fan out upon rotation of the first legs relative to one another, and are adapted to engage with the abdominal wall. The retractor also includes a lifting device that applies a lifting force to the angle-shaped elements. The lifting device includes a unidirectional coupler that applies the lifting force to the angle-shaped elements in the lifting direction, and applies a substantially zero force to the angle-shaped elements in a direction opposite to the lifting direction.

The unidirectional coupler of the fan retractor according to the fifth aspect of the invention reduces the risk of compression injury to the bowel or omentum occurring if a force in the direction opposite to the lifting direction is imposed on the coupling. This can occur if the lifting bar to which the coupling is attached is lowered too far.

A fan retractor according to a sixth aspect of the invention has a pair of angle-shaped elements moveable relative to one another. The angle-shaped elements include first legs disposed in a generally parallel relationship, and second legs extending laterally from the first legs. The second legs fan out upon rotation of the first legs relative to one another, and are adapted to engage with the abdominal wall. At least one of the second legs includes an internal passage. The retractor also includes a lifting means that applies a lifting force to the angle-shaped elements.

The internal passage in at least one of the second legs of the fan retractor according to the sixth aspect of the invention enables the fan retractor to provide aspiration and infusion in its vicinity. Additionally or alternatively, the internal passage can carry an optical fibre through which light to illuminate the treatment site can fed from an external light source.

In a first method of properitoneally lifting the abdominal wall according to the invention, a retractor is provided that includes an angle-shaped element having a first leg, and a second leg extending laterally from the first leg towards a distal end. An incision is made through the abdominal wall to the peritoneal fat layer. The distal end of the second leg is introduced through the incision to separate the peritoneum from the properitoneal fat layer. The second leg is advanced under the peritoneum, and a lifting force is applied to the angle-shaped element.

In a second method according to the invention of properitoneally lifting the abdominal wall, a fan retractor is provided that includes a pair of angle-shaped elements moveable relative to one another. The angle-shaped elements include first legs disposed in a generally parallel relationship, and second legs extending laterally from the first legs towards distal ends. The second legs fan out upon rotation of the first legs relative to one another. An incision is made through the abdominal wall to the properitoneal fat layer. The distal ends of the second legs are introduced through the incision to separate the peritoneum from the properitoneal fat layer. The second legs are advanced under the peritoneum. The first legs are rotated relative to one another to fan out the second legs, and a lifting force is applied to the angle-shaped elements.

In a third method according to the invention of lifting the abdominal wall, a fan retractor is provided that includes a pair of angle-shaped elements moveable relative to one another. The angle-shaped elements include first legs disposed in a generally parallel relationship, and second legs extending laterally from the first legs towards distal ends. The second legs fan out upon rotation of the first legs relative to one another, and have a stiffness in the direction of the first legs that decreases distally from the first legs. An incision is made through the abdominal wall, and the distal ends of the second legs are advanced through the incision. The first legs are rotated relative to one another to fan out the second legs, and the second legs are engaged with the abdominal wall. Finally, a lifting force is applied to the angle-shaped elements.

In a fourth method according to the invention of lifting the abdominal wall using a fan retractor having symmetrical leg opening, a fan retractor is provided that includes a pair of angle-shaped elements moveable relative to one another. The angle-shaped members include first legs disposed in a generally parallel relationship, and linked together such that rotation of one of the first legs through a first angle rotates the other of the first legs through an angle substantially equal and opposite to the first angle. The angle-shaped members also include second legs that extend laterally from the first legs and fan out symmetrically upon equal and opposite rotation of the first legs relative to one another. An incision is made through the abdominal wall, and the second legs are advanced into the incision. The first legs are rotated relative to one another to symmetrically fan out the second leg. The second legs are engaged with the abdominal wall, and a lifting force is applied to the angle-shaped elements.

In a final method according to the invention of lifting the abdominal wall using a fan retractor having a lifting force measuring device, a fan retractor is provided that includes a pair of angle-shaped elements moveable relative to one another. The angle-shaped elements include first legs disposed in a generally parallel relationship, and second legs that extend laterally from the first legs and that fan out upon rotation of the first legs relative to one another. The angle-shaped elements also include a force measuring means for measuring the lifting force. An incision through the abdominal wall, and the second legs are advanced into the incision. The first legs are rotated relative to one another to fan out the second legs, and the second legs are engaged with the abdominal wall. A lifting force is applied to the angle-shaped elements, and the lifting force is observed using the force measuring means.

BRIEF DESCRIPTION OF THE DRAWINGS

FIG. 3A is a perspective view of the preferred embodiment of the second legs of a fan retractor according to the invention in their closed position.

FIG. 3B is a cross sectional view of the first part of the second legs of a fan retractor according to the invention, taken on the line A–A' in FIG. 3A.

FIG. 3C is a cross sectional view of the second part of the second legs of a fan retractor according to the invention, taken on the line B–B' in FIG. 3A.

FIG. 3D is a cross sectional view of the third part of the second legs of a fan retractor according to the invention, taken on the line C–C' in FIG. 3A.

FIG. 3E is a cross sectional view of the fourth part of the second legs of a fan retractor according to the invention, taken on the line D–D' in FIG. 3A.

FIG. 3F is a cross sectional view of the first part of an alternative embodiment of the second legs of a fan retractor according to the invention, in which the first part of the second legs has an oval cross-section.

FIG. 3G is a cross sectional view of the second part of an alternative embodiment of the second legs of a fan retractor according to the invention, in which the first part of the second legs has an oval cross-section.

FIG. 4A is a perspective view of the mounting block and lifting bar adaptor of a simplified version of the fan retractor according to the invention.

FIG. 4B is a cross sectional view of the mounting block and lifting bar adaptor of a simplified version of the fan retractor according to the invention, taken along the line Y–Y'.

FIG. 5A is a perspective view of the preferred embodiment of a fan retractor according to the invention.

FIG. 5B is a plan view of a first embodiment of the additional lifting force indicator of a fan retractor according to the invention.

FIG. 5C is a plan view of a second embodiment of the additional lifting force indicator of a fan retractor according to the invention.

FIG. 6A is a cross sectional view of the preferred embodiment of the fan retractor according to the invention, taken along the line Z–Z' in FIG. 5A.

FIG. 6B is a cross sectional view of the additional lifting force indicating window of a fan retractor according to the invention, taken along the line P–P' in FIG. 6A.

FIG. 6C is a cross sectional view of the indicating tape channel of the fan retractor according to the invention, taken along the line Q–Q' in FIG. 6A.

FIG. 8A is a longitudinal cross section of the abdomen, showing the abdominal wall, the peritoneum, and an incision through the abdominal wall as far as the peritoneum.

FIG. 8B is a longitudinal cross section of the abdomen, showing the abdominal wall, the peritoneum, and the distal ends of the second legs of the fan retractor being inserted through the incision to abut the peritoneum.

FIG. 8C is a longitudinal cross section of the abdomen, showing the abdominal wall, the peritoneum, and the second legs of the fan retractor being advanced between the peritoneum and the abdominal wall and progressively detaching the peritoneum from the abdominal wall.

FIG. 8D is a longitudinal cross section of the abdomen, showing the abdominal wall, the peritoneum, and the fan retractor correctly positioned adjacent to the abdominal wall prior to opening the second legs of the retractor.

FIG. 8E is a plan view of the abdomen showing the fan retractor correctly positioned relative to the center line of the abdomen, prior to opening the second legs of the retractor.

FIG. 8F is a plan view of the abdomen showing the fan retractor symmetrically positioned relative to the center line of the abdomen after the second legs of the retractor have been opened.

FIG. 8G is a longitudinal cross section of the abdomen after the abdominal wall has been lifted by the fan retractor connected to a lifting bar, showing the abdominal wall, the peritoneum, and the fan retractor with the distal parts of its second legs bent to conform with the lifted shape of the anterior abdominal wall.

DETAILED DESCRIPTION OF THE INVENTION

Figure 1:
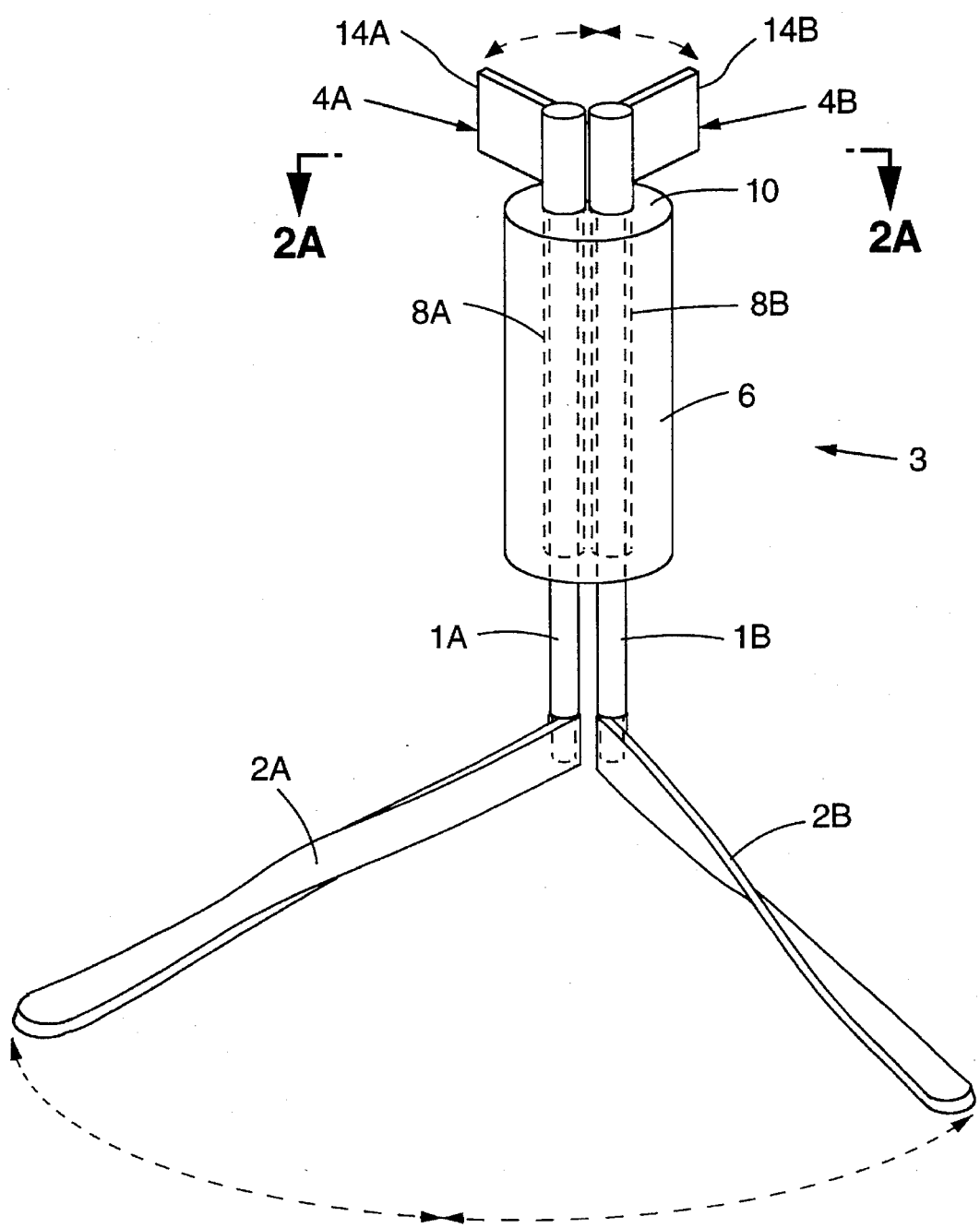
FIG. 1 is a perspective view of a simplified version of a fan retractor according to the invention.

A simplified representation of a fan retractor according to the invention is shown in FIG. 1. The fan retractor 3 has a pair of first legs 1A and 1B, including the leg actuators 4A and 4B, a pair of second legs 2A and 2B, and a mounting block 6 to which the lifting force is applied. The second legs are shown schematically: their specific shape will be described in detail below in connection with FIG. 3A.

The mounting block 6 is cylindrical and includes two axial bores 8A and 8B, symmetrically offset from the axis, that receive the first legs 1A and 1B, respectively. The diameter of the bores is such that the bores snugly receive the first legs with the first legs free to rotate within their respective bores. The mounting block 6 is preferably moulded from a suitable plastic, such as polycarbonate, but other materials, such as stainless steel, can be used.

The first legs 1A and 1B are substantially straight, cylindrical metal rods. In the preferred embodiment, they are made from stainless steel and are about 4.5" long and about 0.15" in diameter.

The leg actuators 4A and 4B are attached to the end of the first legs 1A and 1B, respectively, remote from the second legs, on the opposite side of the first legs from the second legs. The leg actuators bear against the upper face 10 of the mounting block 6 and transfer the lifting force from the upper face 10 of the mounting block 6 to the first legs. The leg actuators are attached to the first legs so that they can withstand a force of several tens of kilograms exerted in the direction of the first legs.

The leg actuators 4A and 4B rotate the first legs. This changes the angular positions of the second legs 2A and 2B with respect to one another. In a fan retractor according to the invention, the second legs 2A and 2B are not capable of independent movement. If one of the second legs, for example 2A, is moved by the operating lever 14A of the leg actuator 4A through a certain angle, the other of the second legs, for example 2B, moves through substantially the same angle in the opposite direction.

In the preferred embodiment, the operating levers 14A and 14B of the leg actuators are on the opposite side of the first legs from the second legs. Moving the operating levers 14A and 14B of the actuators 4A and 4B away from one another brings the second legs towards being parallel to one another (closed position), and bringing the operating levers together splays the second legs apart (open position). This mode of operating is preferred, especially for properitoneal use, since the second legs can be opened, and the peritoneum detached from the anterior fatty layer, simply by squeezing the operating levers together. However, the operating levers may be mounted on the same side of the first legs as the second legs, if desired. Mounted in this way, the operating levers operate in the opposite sense, i.e., squeezing the operating levers together closes the second legs.

Figure 2A:
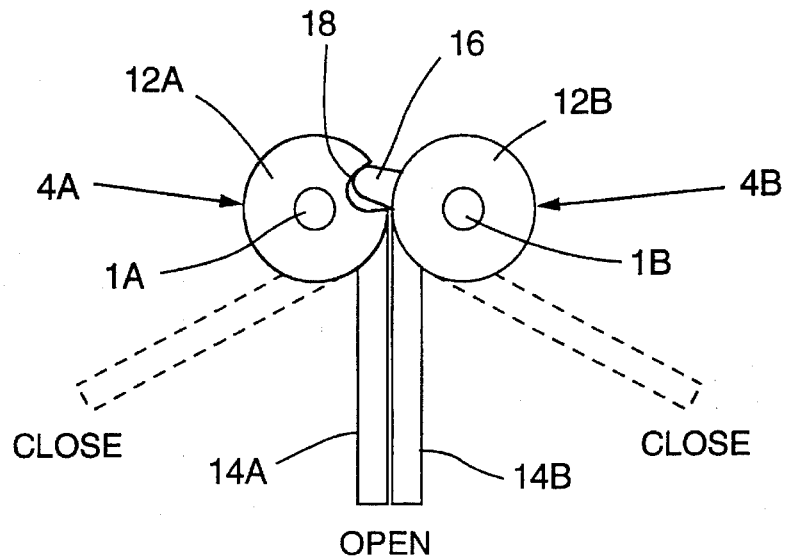
FIG. 2A is a cross sectional view of the leg actuators of a fan retractor according to the invention, taken along the line X–X' in FIG. 1.

The leg actuators 4A and 4B are linked to cause the second legs to move equally and oppositely. Any rotation of one of the leg actuators causes an equal and opposite rotation in the other of the leg actuators. Many known mechanisms exist for providing such relative motion. A cross section of the leg actuators of the preferred embodiment is shown in FIG. 2A. The leg actuators 4A and 4B each comprise a bush 12A, 12B mounted on the respective first leg 1A, 1B, and an operating lever 14A, 14B. The operating levers 14A and 14B translate a lateral movement of the operator's thumb or finger into a rotation of the respective leg actuator 4A and 4B, and of the respective first leg 1A and 1B.

The bush 12B is provided with a peg 16 that engages with a socket 18 provided in the other bush 12A. The location of the peg and the socket can be reversed if desired. The peg and socket arrangement responds to the rotation of either one of the leg actuators 4A and 4B, and imparts an equal and opposite rotation on the other. This arrangement ensures that the second legs 2A and 2B open symmetrically and reduces the risk of one of the second legs inadvertently abutting against, and possibly penetrating, the abdominal wall. This is particularly desirable when the retractor is used properitoneally and the positions of the second legs cannot be seen directly.

Instead of the peg and socket arrangement shown, teeth can be moulded in the outer surfaces of the leg actuators 4A and 4B. Alternatively, the leg actuators can be clamped together in the direction perpendicular to the first legs 1A and 1B, and the resulting friction between them used impart the desired relative motion. Providing one or both of the leg actuators with a high friction surface is desirable in such an arrangement. As a further alternative, the rotation of the first legs themselves can be linked, instead of linking the rotation of the leg actuators.

Figure 2B:
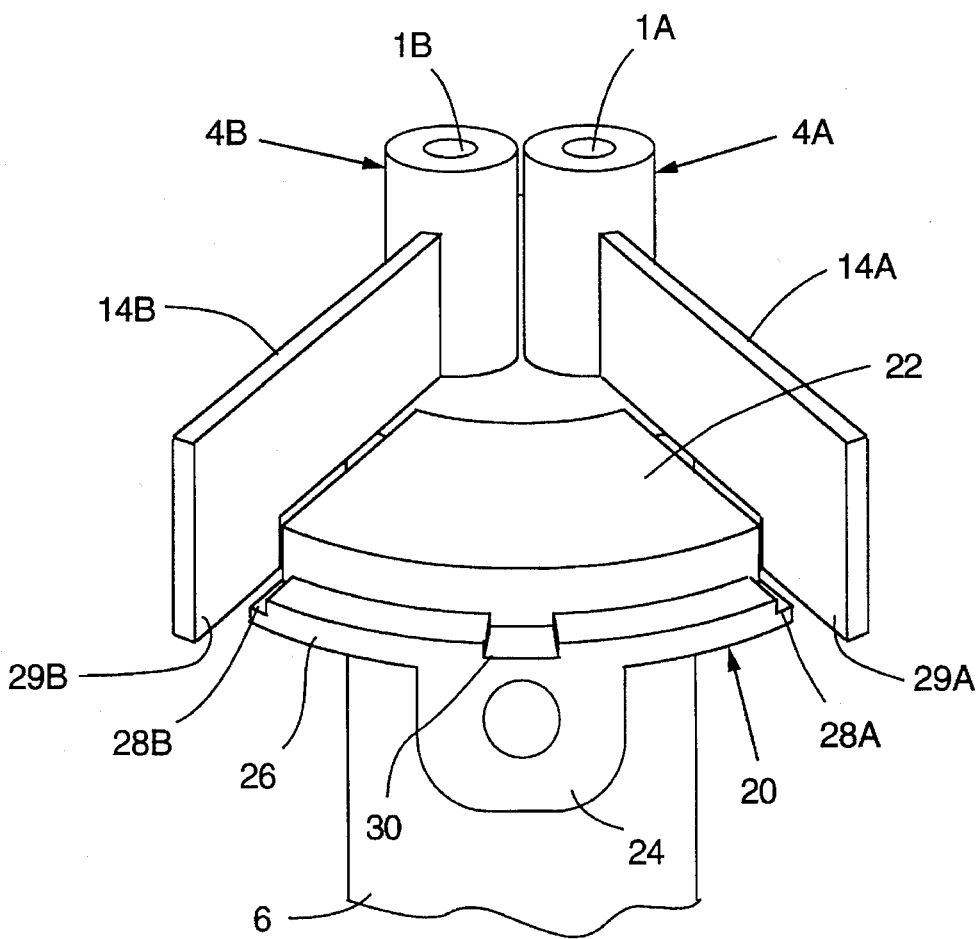
FIG. 2B is a perspective view of the leg actuators of a fan retractor according to the invention.

FIG. 2B shows details of the locking mechanism that holds the operating levers 14A and 14B in their open or closed positions, and hence holds the second legs 2A and 2B in their closed or open positions respectively. The sector 20 is mounted on the mounting block 6 adjacent to the operating levers 14A and 14B. In the preferred embodiment, the sector is moulded integrally with the mounting block. Relative to the operating levers 14A and 14B, the sector is slightly concave, and the operating levers 14A and 14B are biassed against the face 22 of the sector. This causes the sector to apply a frictional force to the operating levers. The frictional force holds the operating levers in any position in which they are set.

The frictional force can be released by pressing the button 24 towards the mounting block 6. The button is attached to, and preferably forms an integral part of, the sector 20. Pressing the button towards the mounting block bends the sector out of contact with the operating levers 14A and 14B, which releases the frictional force.

The skirt 26 of the sector 20 may additionally or alternatively be provided with one, two, or all of the notches 28A, 28B and 30, and the operating levers 14A and 15B provided with the operating lever extensions 29A and 29B. The notches 28A and 28B engage with the operating lever extensions 29A and 29B, respectively, when the operating levers are in the open position, i.e., when the second legs are in their closed position. The notches 28A and 28B lock the operating levers in position, and positively hold the second legs in their closed position. Because the motions of the leg actuators 4A and 4B are linked, one of the notches 28A and 28B may be omitted, if desired.

The notch 30 engages with the operating lever extensions 29A and 29B when the operating levers are in their closed position, i.e., when the second legs are in their open position. The notch 30 locks the operating levers in position, and positively holds the second legs in their open position.

If the notches 28A, 28B and 30 are provided, a clearance must be provided between the sector 20 and the operating levers 14A and 14B to enable the notches to engage with the operating lever extensions 29A and 29B. However, with this arrangement, the skirt 26 applies a frictional force against to the operating lever extensions capable of holding the operating levers, and hence the second legs, in intermediate positions.

FIG. 3A shows a perspective view of the second legs 2A and 2B of a fan retractor according to the invention. FIGS. 3B through 3E show cross sections views of the second legs at various points along their lengths. For both properitoneal use and for conventional use, the stiffness of the second legs in the lifting direction, i.e., in the direction of the first legs, is required to decrease distally from the first legs.

Distally reducing the stiffness of the second legs enables the second legs to bend to conform to the shape of the raised abdomen while having sufficient strength to provide the lifting force necessary. This spreads the lifting force evenly along the length of the second legs, instead of concentrating the lifting force towards their distal ends.

For properitoneal use, second legs that are relatively flat are desirable to make it easy to insert the legs between the peritoneum and the properitoneal fatty layer. Flat legs, i.e., legs that are thin over all of their length, lack sufficient strength to exert the required lifting forces of several tens of kilograms. The inventors have discovered that second legs having an effective thickness that decreases and an effective width that increases distally from the first legs are both easy to insert under the peritoneum and are strong enough to exert the required lifting forces. The increasing thickness of the second legs towards the first legs acts as a wedge to detach the peritoneum progressively from the properitoneal fatty layer as the second legs are advanced under the peritoneum. The distally reducing thickness of the second legs also causes the stiffness of the second legs to reduce distally, which is desirable to enable the second legs to conform with the shape of the raised abdomen. The distally increasing width of the second legs helps maintain a more constant pressure against the peritoneum along the length of the second legs.

It is also desirable that the second legs form a relatively compact shape when in their closed position to reduce the size of the incision required to introduce the second legs into the abdomen, either conventionally or properitoneally.

The preferred design for the second legs that meets the requirements just stated is shown in FIGS. 3A through 3E. Both the cross sectional area and the cross sectional shape of the second legs change distally from the first legs 1A and 1B.

The preferred second legs can be regarded as having four distinct parts. In the first part 40 of the second legs, close to the first legs, the cross section of each second leg is substantially semi-circular, as shown in FIG. 3B. In the first part of the second legs, the second legs have an appreciable thickness $t_1$ in the direction of the first legs. This provides considerable beam strength and stiffness, measured in the direction of the first legs, so that the required retraction force can be exerted. The semicircular cross section enables the two second legs to fit together to form a compact shape when the retractor is in its closed position.

In the second part 42 of the second legs, the thickness $t_2$ Of the second legs 2A and 2B remains the same as the thickness $t_1$ of the first part 40, but the width $w_2$ of the second legs progressively reduces as the cross section changes from semi-circular to rectangular. Figure 3C shows the cross section of the second legs towards the distal end of the second part where the outer surfaces 48A and 48B of the second legs are still slightly curved. At the distal end of the second part, the outer surfaces 48A and 48B are substantially straight. The length $y_2$ of the major axis of the rectangular cross section is substantially equal to the diameter d of the semicircular cross section of the first part 40 of the second legs, shown in FIG. 3B.

In the second part 42, the second legs have an appreciable thickness $t_2$ in the direction of the first legs. The beam strength and stiffness of the second legs, although appreciable, is less than in the first part 40 because the width $w_2$ of the second part is less than the width $w_2$ of the first part. The rectangular cross section enables the second parts of the second legs to fit together to form a compact shape when the retractor is in its closed position, as shown in FIG. 3C.

In the third part 44 of the second legs, the second legs have the same rectangular cross section as the distal part of the second part 42, but the second leg is twisted progressively through about 90 degrees over the length of the third part. The cross section of the legs about half-way along the third part, at which point the legs are twisted through about 45 degrees, is shown in FIG. 3D. The dimensions, $x_3$ and $y_3$ of the minor and major axes, respectively, of the rectangular cross section remain the same as the dimensions $x_2$ and $y_2$ of the minor and major axes, respectively, of the rectangular cross section in the second part. Along the third part distally from the second part, the twisting the second legs causes the effective thickness, $t_3$ of the leg to decrease and the effective width $w_3$ of the leg to increase.

Both of the second legs are twisted in the same direction through the same angle so that they will fit together to form a compact shape when the retractor is in its closed position. The two second legs are not identically twisted, however. So that the fourth part 46 of one of the second legs can fit on top of the fourth part of the other of the second legs when the retractor is in its closed position, the twist in one of the second legs is slightly offset in the direction of the first legs, and the twist in the other of the second legs is offset in the direction opposite to the direction of the first legs. Alternatively, the second legs can be made with identical twists, and be mounted on the first legs so that one forms an angle of slightly more than 90 degrees with its first leg, and the other forms an angle of slightly less than 90 degrees with its first leg.

In the third part 44, the second legs have an effective thickness $t_3$ in the direction of the first legs that progressively decreases distally from the first legs. Hence, the beam strength and stiffness of the second legs also decrease distally from the first legs. Finally, the insertion height $h_3$ of the second legs when the retractor is in its closed position progressively decreases distally from the first legs.

In the fourth part 46 of the second legs, the second legs have the same rectangular cross section as the distal part of the second part 42, but the cross section is substantially perpendicular to the cross section of the second part, as shown in FIG. 3E. The dimensions, $x_4$ and $y_4$ of the minor and major axes, respectively, of the rectangular cross section remain the same as the dimensions $x_2$ and $y_2$ of the minor and major axes, respectively, of the rectangular cross section in the second part.

In the fourth part 46, the second legs have an effective thickness $t_4$ in the direction of the first legs that remains substantially constant and equal to the physical thickness $y_4$ of the second legs. Hence, the beam strength and stiffness of the second legs are also substantially constant in the fourth part, and are considerably less than in the first and second parts, and in the part of the third part proximal to the first legs. The effective width $w_4$ of the second legs in the fourth part is substantially equal to the physical width $x_4$ of the legs, and is considerably greater than in the first and second parts. This considerably reduces the pressure that the fourth parts of the second legs of the retractor exert per square centimeter of abdominal wall. Finally, the insertion height $h_4$ of the fourth part of the second legs when the retractor is in its closed position is substantially equal to twice the physical thickness $y_4$ of the second legs as a result of the fourth parts of the second legs stacking on top of one another. This dimension is relative small and makes it easy to insert distal ends of the second legs of the retractor between the peritoneum and the peritoneal fat layer. Also, the distal ends 49A and 49B of the second legs are rounded to further ease insertion.

In the preferred embodiment, the four parts of the second leg are approximately equal to one another in length. However, the relative lengths of the four parts can be varied to achieve a better stiffness versus distance from the first legs characteristic.

In the preferred embodiment, the first part 40 of the second legs has a semicircular cross section. An alternative oval cross section is shown in FIG. 3F, with the corresponding cross section of the second part 42 shown in FIG. 3G. The cross sections of the third and fourth parts are substantially the same as the cross sections of the third and fourth parts shown in FIGS. 3D and 3E, respectively.

Second leg blanks having the required thickness profile for the preferred embodiment, but lacking a twisted third part 44, can be molded using a relatively simple mold. From the second leg blanks, second legs with the flat side of the first part on the left, like second leg 2A, and second legs with the flat side of the first part on the right, like second leg 2B, can be made. After a second leg blank has been moulded, it is placed in a twisting jig and supported at the distal end of its second part 42. The fourth part 46 is clamped in a rotating port of the jig. The third part of the leg is heated to soften it, and the rotating part of the jig is rotated through about 90 degrees to impart the desired twist in the third part 44 of the leg. The leg is left to cool before it is removed from the jig. The orientation of the flat side of the first part of the leg in the twisting jig determines whether a type-2A leg or a type-2B leg is made. The twisting direction is the same for both types of leg.

It is preferred, however, to make a more complex tool and to mold the second legs the required twist. With considerably more complex tools, second legs can be made having a stiffness versus distance from the first legs characteristic that is fully optimized along the length of the leg for its intended application.

The mounting block 6 can be provided with a variety of attachments suitable for coupling to known lifting bars. In the preferred embodiment, the mounting block is provided with a dovetail connector 50, as shown in FIGS. 4A and 4B. The dovetail connector is trapezoidal, with its parallel sides 52 and 54 perpendicular to the lifting direction, and its long parallel side 52 spaced from its short parallel side 54 in the lifting direction. The non-parallel sides, 56 and 58, form an acute angle with the front face 60. The arrangement of non-parallel sides forming an acute angle with the front face forms a positive lock with a dovetail slot 62, which is a female version of the dovetail connector 50, formed in the lifting bar adaptor 64. The lifting bar adaptor is attached to the lifting bar by conventional means (not shown).

The dovetail connector 50 and dovetail slot 62 form a unidirectional lifting force coupling. The dovetail slot and dovetail connector will transmit to the mounting block 6 a lifting force applied to the lifting bar adaptor 64 in the direction indicated by the arrow 66. A force applied in the direction opposite to that shown by the arrow 66 causes the dovetail slot to disconnect from the dovetail connector, which prevents the coupling from transmitting any force in the opposite direction.

When the retractor is used for lifting, the retractor is inserted into the abdomen and the dovetail connector 50 is engaged in the dovetail slot 62 in the lifting bar adaptor 64. The lifting bar is then raised to lift the abdominal wall, and is maintained in position during treatment. After treatment has been completed, the lifting bar is progressively lowered to return the abdominal wall to its normal position. At a point at which the force between the dovetail connector 50 and the dovetail slot 62, measured in the lifting direction, fails below zero, the dovetail connector automatically disconnects from the dovetail slot. This prevents the reverse force from being transmitted to the retractor, and indicates to the operator that the lifting bar has been lowered far enough. The dovetail connector provides a safety mechanism that prevents compression injury to the bowel if the lifting bar is lowered too far.

FIG. 5A is a perspective view of the preferred embodiment of a fan retractor 100 including all of the aspects of the invention. In the preferred embodiment, the first legs 101A and 101B are extended by about 1" (25 mm) distally from the leg actuators 104A and 104B. The extended parts of the first legs are bent through about 90 degrees. The part of each of the first legs distal from the bend is inserted into an axial bore in the first part of the respective second leg. This arrangement is stronger than the arrangement shown in FIG. 1.

Also, in the preferred embodiment, the first legs 101A and 101B pass through offset axial bores in the cylindrical lower mounting block 168, which is slidably mounted in the lower part of the bore of the mounting sleeve 170. The main mounting block 106 is spring mounted in the upper part of the bore of the mounting sleeve 170, as will be described in connection with FIG. 6A below. The dovetail connector 150 is mounted on the mounting sleeve 170, instead of directly on the mounting block 150. The main mounting block can rotate relative to the mounting sleeve and the dovetail connector. This enables the second legs to face in any direction relative to the lifting bar prior to lifting. Once lifted, the lifting force prevents the main mounting block from rotating relative to the mounting sleeve, and holds the legs in the position in which they were set prior to lifting.

When the preferred embodiment of the retractor is used to retract the abdominal wall, the lifting force is applied to the mounting sleeve 170 through the dovetail connector 150. The spring mounting of the main mounting block 106 enables the relative axial positions of the mounting sleeve and main mounting block to change in response to the lifting force. The mounting sleeve moves relative to the scale 172 marked on the cylindrical surface of the mounting block, which indicates the magnitude of the lifting force. The lifting force indicator thus provided enables the lifting force to be monitored during the lifting process, and reduces the risk that an excessive lifting force will be used.

Alternatively, the lifting force scale (not shown) can be marked on the surface of the mounting sleeve 170 and a pointer (not shown) attached to the main mounting block 106 can move against the scale to indicate the lifting force.

The lifting force scale on the cylindrical surface of the mounting sleeve 170 or of the mounting block 106 is most easily seen from the side. The preferred embodiment includes an additional lifting force indicator 174 on the end face 178 of the mounting block to enable the lifting force to be monitored easily looking from above. The additional lifting force indicator is shown in detail in FIGS. 5B and 5C. The additional lifting force indicator includes a window 176 in the end face 178 of the mounting block. A tape 180 moves in the window 176 in response to the motion of the mounting block relative to the mounting sleeve as a result of the lifting force. In the variation shown in FIG. 5B, the tape is marked with a reference mark 182 that moves against the scale 184 marked in the window 176, adjacent to the tape 180. In the variation shown in FIG. 5C, the tape is marked with the scale 186 that moves against the reference mark 188 marked in the window 176, adjacent to the tape.

The assembly of the main mounting block 106, the lower mounting block 168, and the mounting sleeve 170, and details of the additional lifting force indicator are shown in FIG. 6A. The mounting sleeve 170 is a tubular piece of plastic or metal having a bore. The lower part 190 of the bore receives the lower mounting block 168. A pin 171 passes through a radial bore in the lower mounting block between the first legs, and engages with a groove in each of the first legs to axially locate the lower mounting block relative to the first legs. In FIG. 6A, the groove 173A in the first leg 101A is shown.

The upper part 192 of the bore, which, in the preferred embodiment, has a larger diameter than the lower part 190, receives the main mounting block 106. Separating the upper and lower parts of the bore is the lip 194, which provides an end-stop for upward movement of the lower mounting block 168 in the mounting sleeve 170. The lip 194 also supports the nylon washer 196 on which the lower end of the coil spring 198 rests. The lower surface 202 of the main mounting block 106 rests on the upper end of the coil spring 198, with a circumferential groove 200 in the lower surface receiving the spring.

A lifting force applied to the dovetail connector 150 on the mounting sleeve 170 is transferred through the lip 194, the nylon washer 196, and the coil spring 198 to the upper mounting block 106, and thence to the first and second legs of the retractor. Compression of the spring 198 in response to the lifting force allows the main mounting block 106 to move relative to the mounting sleeve 170, and causes the top rim 204 of the mounting sleeve to juxtapose a different point on the scale 172, which indicates the lifting force.

The main mounting block 106 includes an upper lifting force indicator passage 210 machined or moulded into it. The passage 210 has an exit in the lower face 202 of the main mounting block, and continues distally from the lower face in a substantially straight line parallel to the curved side of the upper mounting block. Proximate to the window 176, the passage has a curved portion 212 that curves to form an arc in the window, followed by a straight portion 213 that returns at least part-way back towards the lower face 202.

The tape 180 runs through the passage 210. One end of the tape is attached to the mounting sleeve 170, preferably adjacent to the lip 194. The straight part of the passage 210 preferably has a cross section that curves across the width of the tape, as shown in FIG. 6C, to impart a stiffness to the tape.

The window 176 has a width $w_w$ that is narrower than the width $w_t$ of the tape 180, as shown in FIG. 6B. This enables the lips 214 and 216 to guide the tape in the curved part 212, where part of the wall of the passage is missing because of the window 176.

Compression of the spring 198 in response to the lifting force allows the main mounting block 106 to move relative to the mounting sleeve 170. This causes the tape 180 to move relative to the passage 210, and the reference mark 182 (or graduations 186) on the tape to move relative to the graduations 184 (or reference mark 188) in the window 176. The movement of the tape relative to the window indicates the lifting force.

Solid second legs are shown in FIG. 3A. The second legs may alternatively be provided with an arrangement of one or more internal passages, such as the arrangement of a longitudinal passage connecting to one or more transverse passages connecting to the surface of the leg shown in FIGS. 7A–7C. An internal passage can be dedicated to a specific purpose, or can be made to receive a variety of inserts that are plugged into the internal passage to provide different capabilities, as required.

Figure 7A:
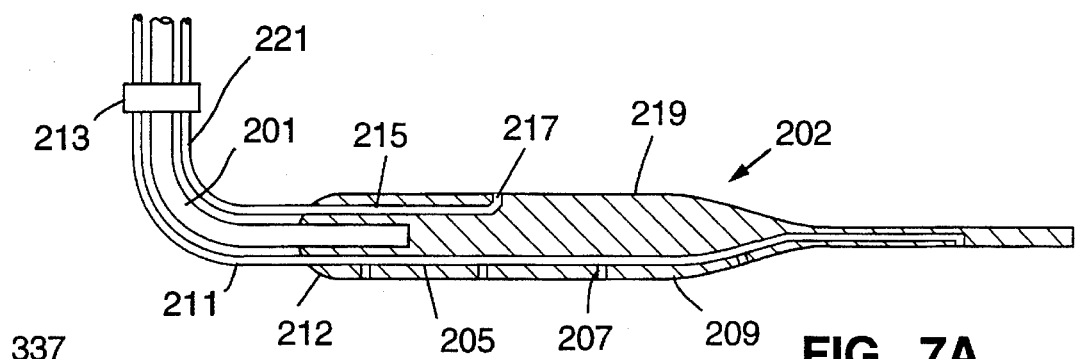
FIG. 7A is a longitudinal cross sectional view of a second leg of a fan retractor according to the invention. The second leg has an internal bore arrangement providing aspiration and/or irrigation.
Figure 7B:
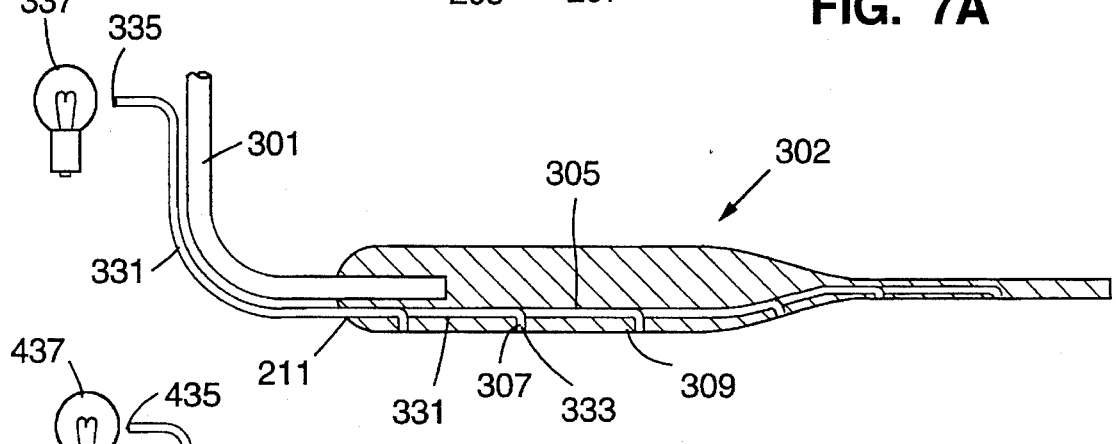
FIG. 7B is a longitudinal cross sectional view of a second leg of a fan retractor according to the invention. The second leg has an internal bore arrangement providing working lighting using optical fibres.

FIGS. 7A and 7B show two examples of internal passage arrangements in which connections are made to an internal passage at the end of the second leg proximal to the first leg. Second legs can be also made with different internal passage arrangements, including, for example, arrangements with more or fewer longitudinal passages, with more or fewer transverse passages, and/or with transverse passages connecting to the side surfaces of the second legs.

FIG. 7A shows a second leg 202 attached to a first leg 201. The second leg 202 has an internal passage arrangement with two longitudinal passages 205 and 215. The longitudinal passage 205 is connected to a plurality of transverse passages, including the transverse passage 207, connecting to the lower surface 209 of the second leg. A pipe 211 is plugged into the proximal end 212 of the second leg to connect to the longitudinal passage 205. The pipe 211 is run up the outside of the first leg 201 to a suitable connection (not shown). The pipe 211 is retained in position relative to the first leg 201 by the clamp 2 13.

The longitudinal passage 215 is connected to the single transverse passage 217 in the upper surface 219 in the second leg. The pipe 221 connects to the longitudinal passage 215 and runs up the outside of the first leg 201, and is retained by the clamp 213.

The internal passage arrangement can be connected to a vacuum line, which enables blood and other fluids to be aspirated from the vicinity of the fan retractor. Such an arrangement can also be used to aspirate the smoke generated by electrocautery, a process commonly used in laparoscopic procedures.

The internal passage arrangement can be connected to a suitable syringe, pump, or water line, so that fluids can be infused into the vicinity of all or parts of the second legs. The fluids can be infused into the abdomen if the fan retractor is used conventionally, or into the space between the peritoneum and the properitoneal fatty layer, if the fan retractor is used properitoneally. For example, saline can be infused for irrigation. In another example, a suitable insufflation gas can be infused for pneumoperitoneum. In procedures using local anaesthesia, a spray of anaesthetic can be sprayed into the abdomen from the fan retractor.

In the arrangement with two longitudinal passages and connecting transverse passages shown in FIG. 7A, the longitudinal passage 215 and transverse passage 217 can be used for infusion, and the longitudinal passage 205 and plurality of transverse passages, such as the transverse passage 207, can be used for aspiration.

In the embodiment of a fan retractor having second legs with an internal passage arrangement shown in FIG. 7B, the second leg 302 is attached to the first leg 301. The second leg has a longitudinal passage 305, connected to a plurality of transverse passages, including the transverse passage 307, that connect to the lower surface 309 of the second leg. A plurality of optical fibres 331 is inserted into the longitudinal passage 305 through the proximal end 211 of the second leg. Individual fibres, such as the fibre 333, or groups of fibres, are brought to the lower surface 309 through the transverse passages, such as the transverse passage 307.

The proximal end 335 of the plurality of optical fibres is connected to a suitable light source 337. Light from the light source is emitted from the ends of the fibres, such as the end of the fibre 333, in the lower surface 309 of the second legs and provides working light for the surgeon to treat the tissue being treated. The peritoneum is sufficiently translucent that light emitted from optical fibres in the second legs of the fan retractor will provide adequate working light even when the retractor is inserted properitoneally.

Instead of inserting a plurality of optical fibres into passages in the second leg, the optical fibres can be molded integrally with the second leg as part of the process of molding the second leg blanks.

Figure 7C:
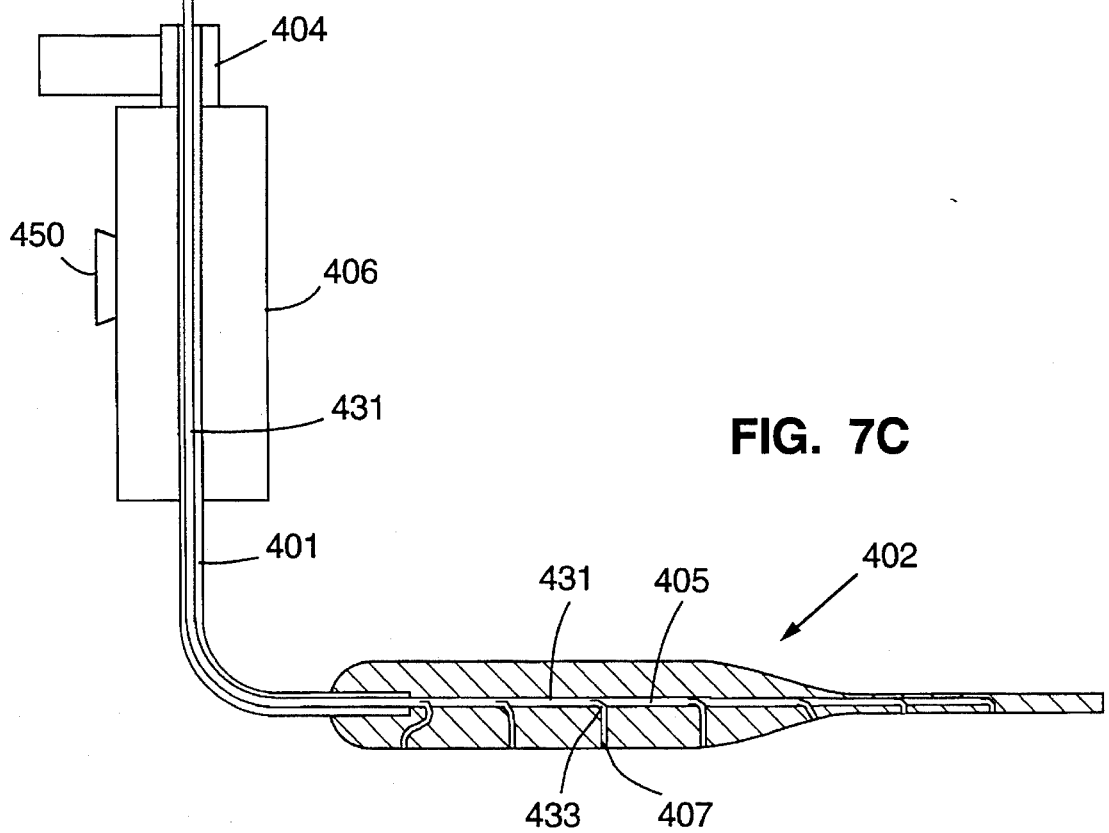
FIG. 7C is a longitudinal cross sectional view of a second leg of a fan retractor according to the invention. The second leg has an internal bore arrangement providing working lighting using optical fibres brought into the second leg through a bore in the first leg.

FIG. 7C shows an alternative arrangement in which the first leg 401 is formed using a hollow tube, the bore of which connects to the internal passage arrangement of the second leg. In the example shown, the plurality of optical fibres 431 passes through the bore of the first leg into the longitudinal passage 405, and individual fibres, such as the fibre 433, are brought out to the lower surface 409 of the second legs through a plurality of transverse passages, such as the passage 407. Otherwise, the construction of the second leg 402 is similar to the second leg 302 in FIG. 7B, and will not be described further.

The first leg 401 is extended through the leg actuator 404 to allow the plurality of optical fibres 431 to emerge from the bore of the first leg thus exposed. FIG. 7C shows a simple form of the fan retractor that lacks a lifting force indicator (FIGS. 5 and 6A). In fan retractors equipped with lifting force indicators (FIG. 6A), the additional lifting force indicator has to be relocated to provide room for the plurality of optical fibres.

FIG. 7C shows an embodiment of the fan retractor having a plurality of optical fibres inserted in the internal passages of the second leg 402. Alternative versions of the embodiment of FIG. 7C can be made in which the internal passages are used for infusion or aspiration. In these, the infusion or aspiration pipe (similar to the pipes 211 and 221 in FIG. 7A) can be run inside the bore of the first leg 410. If the second leg has multiple internal passages, multiple pipes and optical fibres can be run through the bore of the first leg.

A method of using a fan retractor according to the invention properitoneally to lift the abdominal will next be described.

Figure 8A:
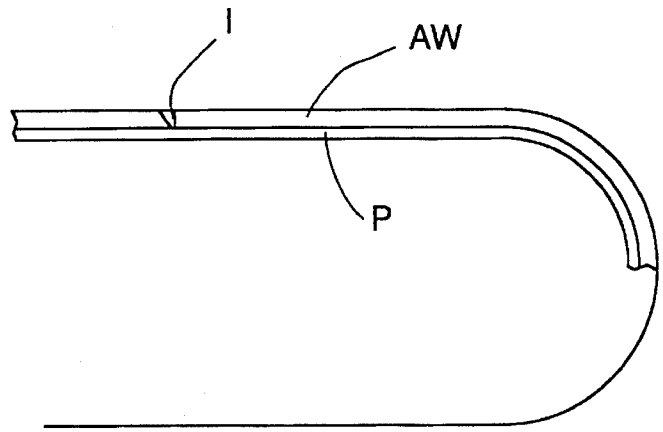
FIGS. 8A through 8G illustrate the method according to the invention of using a fan retractor according to the invention properitoneally to lift the abdominal wall.

An incision I, 0.4"–0.8" (10–20 mm) long is made in a suitable location in the abdominal wall AW, as shown in FIG. 8A. The incision is made through the skin, the subcutaneous fat, muscle and fascia, until the properitoneal fat layer is reached, just short of the peritoneum P.

Figure 8B:
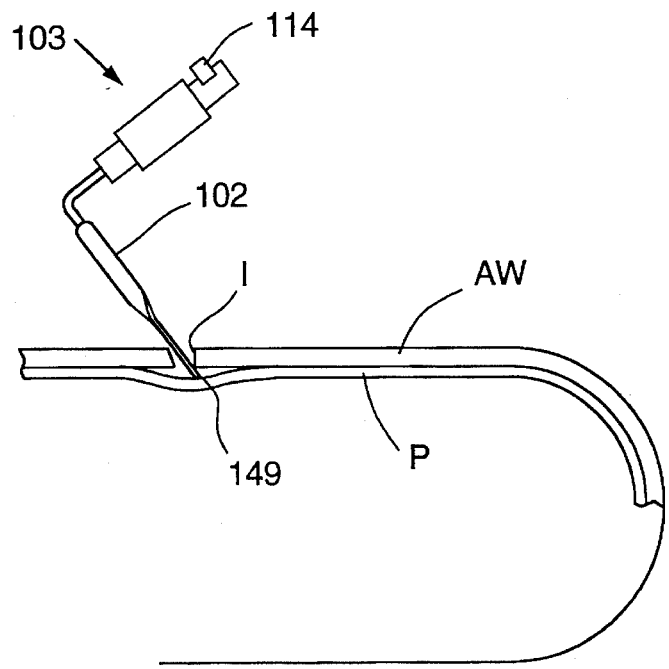
Figure 8C:
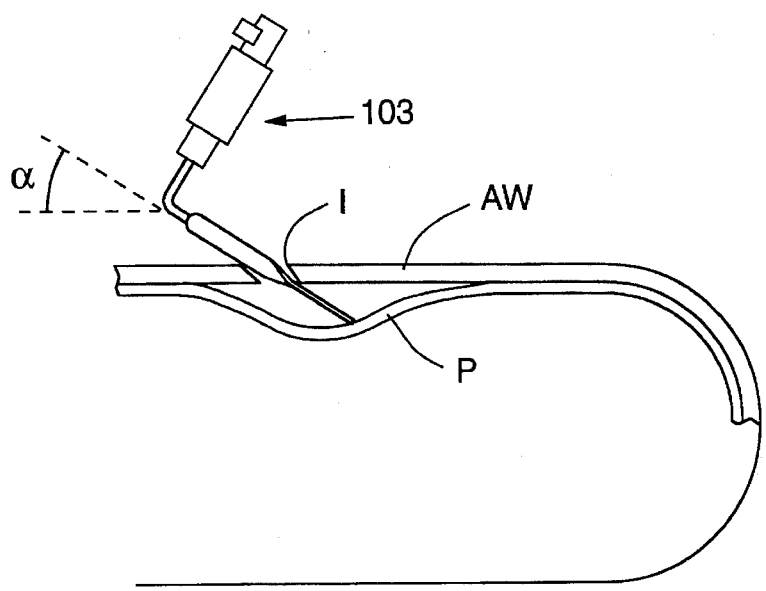

The operating levers 114 of the fan retractor 103 are manipulated to bring the second legs 102 fan retractor to their closed state if they are not in this state already. The distal ends 149 of the second legs are then inserted into the incision I and pushed through the incision until they abut against the peritoneum P. The pressure of the wide, gently curved distal ends of the second legs against the peritoneum detaches the peritoneum from the properitoneal fatty layer without piercing the peritoneum, as shown in FIG. 8B. The distal ends 149 of the second legs are worked into the space between the peritoneum and the properitoneal layer. The retractor is then advanced along the center line CL of the abdomen (FIG. 8E), keeping the angle α between the second legs and the abdominal wall as small as possible to minimize detachment of the peritoneum, as shown in FIG. 8C. Advancing the second legs progressively detaches the peritoneum from the properitoneal layer.

Figure 8D:
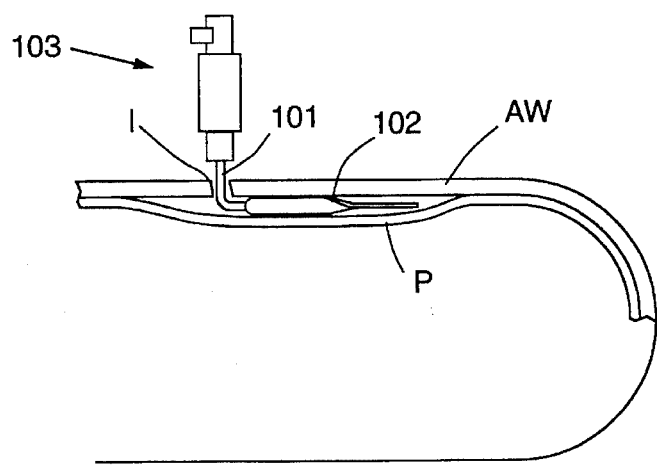
Figure 8E:
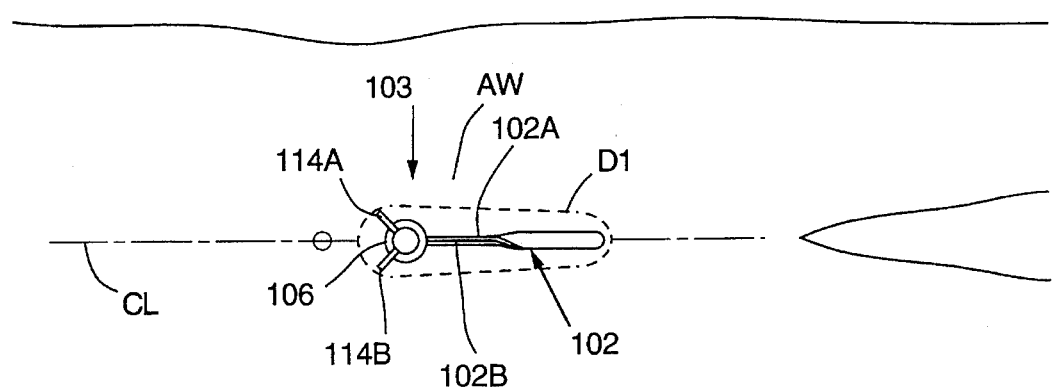

The first legs 101 abutting against the incision I limits the advancing of the second legs 102, as shown in FIG. 8D. The orientation of the second legs relative to the center line CL of the abdomen is checked, and the second legs are reoriented if necessary to align them along the center line (FIG. 8E). Since the second legs 102 have a fixed orientation relative to the main mounting block 106, orientation marks on the main mounting block can be used to indicate the direction of the second legs. The outline of the part of the peritoneum detached from the properitoneal layer is shown by the broken line $D_1$ in FIG. 8E.

Figure 8F:
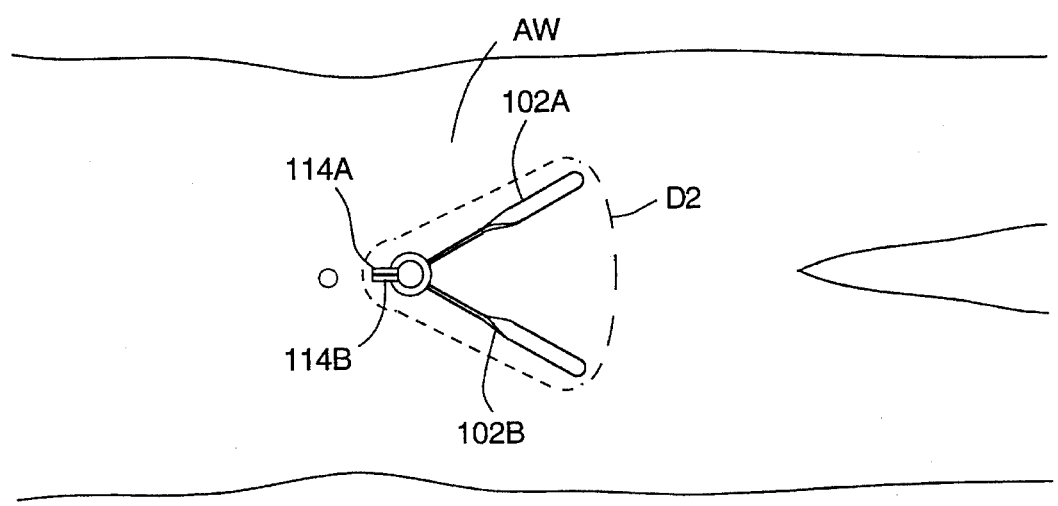

The operating levers 114A and 114B are then squeezed together to force the second legs 102A and 102B apart, as shown in FIG. 8F. In moving apart, the second legs detach more of the peritoneum from the properitoneal layer, as shown by the dotted line $D_2$. While squeezing the operating levers, the orientation of the main mounting block 106 is observed to ensure that asymmetrical resistance to the opening of the second legs does not skew the symmetrical placement of the second legs relative to the center line CL. Since the second legs open symmetrically with respect to the main mounting block, any skewing of the second legs can be observed as rotation of the main mounting block. An appropriate torque applied to the main mounting block can be used to correct any skewing that occurs, and ensure that the second legs are symmetrically placed.

Figure 8G:
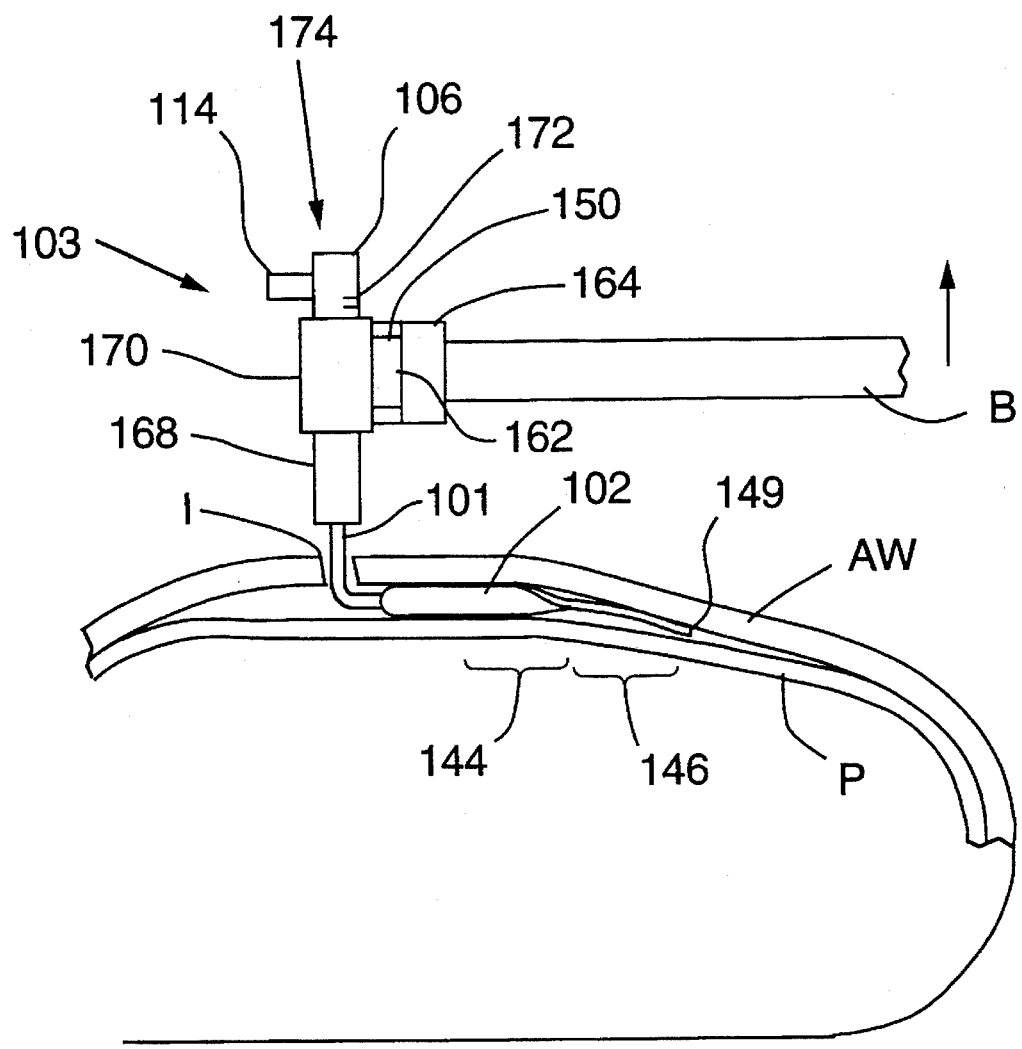

The dovetail connector 150 is coupled to the dovetail slot 162 on the lifting bar adaptor 164, as shown in FIG. 8G. The lifting bar adaptor is attached to the lifting bar B by conventional means (not shown). The main mounting block can rotate relative to the mounting sleeve, so the orientation of the lifting bar relative to the second legs may be changed from that shown, if desired. The lifting bar B is then raised progressively while watching one of the lifting force indicators, the scale 172 on the cylindrical wall of the main mounting block 106, or the additional lifting force indicator 174 in the end face of the main mounting block. If the lifting force comes close to the allowable limit for the procedure, the lifting force can be reduced by reducing the rate of lifting, or stopping the lifting altogether.

As the lifting force applied to the retractor increases, and the abdomen becomes more curved as a result of being lifted, the third and fourth parts 144 and 146 of the second legs bend to conform with the shape of the inside of the abdominal wall, as shown in FIG. 8G. The bending and the relatively large width of the distal parts of the second legs, and the symmetrical placing of the second legs within the abdomen, substantially reduce the risk of the ends 149 of the second legs traumatizing or penetrating the abdominal wall AW.

Once the required amount of lifting has been obtained, the lifting bar B is locked in position, and the treatment procedure is carried out. The incision I may be carried through the peritoneum, and used to insert endoscopes or other instruments into the abdomen. The incision I can be put to further use because the first legs 101 of the retractor occupy only a relatively small part of the incision.

If the second legs of the retractor have longitudinal passages, these may be used during the treatment procedure to provide illumination of the treatment area, and infusion and aspiration of the properitoneal area.

After treatment has been completed, the lifting bar B is progressively lowered to return the abdomen to its normal state. When the lifting force on the dovetail connector 150 falls to zero, the dovetail connector disconnects from the dovetail slot 162. This informs the operator that the lifting bar has been lowered far enough, and also prevents the lifting bar from driving the retractor into the abdomen and causing compression injury to the underlying bowel.

The operating levers 114 are moved apart to bring the second legs 102 together once more. The fan retractor 103 is then manipulated to withdraw the second legs from under the peritoneum through the incision I.

The properitoneal retraction method according to the invention is preferably practiced using a fan retractor according to the invention, described above, which is specially designed for this purpose. However, the fan retractor according to the invention is not a requirement for practicing the properitoneal retraction method according to the invention. The method can be practiced using other suitable retractors.

Properitoneal retraction is preferred because interposing the peritoneum between the retractor and the underlying bowel and omentum prevents the retractor from snagging the bowel or omentum. This makes the process of inserting the retractor easier, and less risky.

The fan retractor according to the invention is not limited to properitoneal use. Most of the advantages conferred by the fan retractor according to the invention can also be obtained when the fan retractor is used in the abdomen to exert its lifting force against the posterior face of the peritoneum.

The method set forth above can easily be adapted for conventional use. The incision I is carried through the peritoneum. The abdomen is preferably insufflated before the second legs of the retractor is inserted through the incision. Insufflation provides a clearance between the second legs of the retractor and the underlying bowel and omentum. A third incision is required for an endoscope to observe placement of the second legs.

When the second legs are inserted into the abdomen, care must be taken to ensure that they are kept as close to the abdominal wall as possible to reduce the chance of snagging bowel or omentum. The insertion process and the leg spreading process must be carried out under continuous observation to check for snagging. If snagging occurs, the second legs must be withdrawn, at least partially, to release the snag, and the insertion process recommenced.

Providing illumination in the vicinity of the second legs using a plurality of optical fibres inserted into internal passages in the second legs makes it easier to see snags than conventional illumination methods.

Once the second legs have been fully inserted and it is confirmed that they do not snag anything, the fan retractor is used to lift the abdominal wall, as described above.

We claim:

1. Apparatus for atraumatically and properitoneally lifting the abdominal wall by applying a lifting force of greater than ten kilograms thereto, the abdominal wall including a properitoneal fat layer and a peritoneum, the apparatus comprising:

(a) a pair of angle-shaped elements moveable relative to one another, the angle-shaped elements including:
  (1) first legs disposed in a generally parallel relationship, the first legs having a first leg direction, and
  (2) elongate second legs extending from the first legs towards distal ends in a second leg direction, substantially perpendicular to the first leg direction, the second legs:
    (i) fanning out upon rotation of the first legs relative to one another,
    (ii) being shaped to include a broad lifting surface substantially perpendicular to the first leg direction,
    (iii) being adapted for separating the peritoneum from the properitoneal fat layer by insertion therebetween to engage the lifting surface with the properitoneal fat layer,
    (iv) having an effective thickness in the first leg direction that decreases in the second leg direction from a maximum adjacent the first legs, and
    (v) having an effective width perpendicular to the first leg direction and to the second leg direction that increases in the second leg direction to a maximum adjacent the distal ends, the effective width being plural times the effective thickness adjacent the distal ends; and (b) lifting force applying means for applying the lifting force to the first legs in a direction substantially parallel to the first leg direction.

2. Apparatus for properitoneally lifting the abdominal wall by applying a lifting force thereto, the abdominal wall including a properitoneal fat layer and a peritoneum, the apparatus comprising:

(a) a pair of angle-shaped elements moveable relative to one another, the angle-shaped elements including:

(1) first legs disposed in a generally parallel relationship, the first legs having a first leg direction, and (2) elongate second legs extending from the first legs in a second leg direction, substantially perpendicular to the first leg direction, the second legs:

(i) fanning out upon rotation of the first legs relative to one another; and (ii) each having a length and a cross-section, wherein:

the cross-section is substantially semi-circular in a first part of the length of the second legs, proximal to the first legs, the semi-circular cross-section having a diameter that is substantially parallel to the first legs, the cross-section gradually changes to substantially oblong in a second part of the length of the second legs, adjacent to the first part, the oblong cross-section having a long axis that is substantially parallel to the first legs, and the cross-section remains substantially oblong in a third part, adjacent to the second part, and in a fourth part, adjacent to the third part, of the length of the second legs, the oblong cross-section having a long axis that progressively changes from substantially parallel to the first legs to substantially perpendicular to the first legs over the third part, and remains substantially perpendicular to the first legs in the fourth part to provide an effective thickness in the first leg direction that decreases in the second leg direction from a maximum adjacent the first legs; and (b) lifting force applying means for applying the lifting force to the first legs in a direction substantially parallel to the first leg direction.

3. The apparatus of claim 2, wherein the cross-section of the first part of the length of the second leg of the one of the angle-shaped elements is a mirror image of the cross-section of the first part of the length of the second leg of the other of the angle-shaped elements.

4. The apparatus of claim 2, wherein the long axis of the oblong cross-section of the second legs of one of the angle-shaped elements changes from substantially parallel to the first legs to substantially perpendicular to the first legs in a first direction, and the long axis of the oblong cross-section of the second legs of the other of the angle-shaped elements changes from substantially parallel to the first legs to substantially perpendicular to the first legs in the first direction.

5. The apparatus of claim 2, wherein the second legs of the angle-shaped elements have a closed position wherein the second legs are substantially parallel to one another, the first and second parts of the length of the second leg of one of the angle-shaped elements being substantially parallel to the first and second parts of the length of the second leg of the other of the angle-shaped elements in a first plane, and the fourth part of the length of the second leg of the one of the angle-shaped element being substantially parallel to the fourth part of the length of the second leg of the other of the angle-shaped elements in a plane substantially perpendicular to the first plane.

6. The apparatus of claim 2, wherein the first part, the second part, the third part, and the fourth part of the lengths of the second legs each have a length approximately equal to one-fourth of the length of the second legs.

7. Apparatus for properitoneally lifting the abdominal wall by applying a lifting force thereto, the abdominal wall including a properitoneal fat layer and a peritoneum, the apparatus comprising:

(a) a pair of angle-shaped elements moveable relative to one another, the angle-shaped elements including:

(1) first legs disposed in a generally parallel relationship, the first legs having a first leg direction, and (2) elongate second legs extending from the first legs in a second leg direction, substantially perpendicular to the first leg direction, the second legs:

(i) fanning out upon rotation of the first legs relative to one another; and (ii) each having a length and a cross-section, wherein:

the cross-section is substantially semi-circular in a first part of the length of the second legs, proximal to the first legs, the semi-circular cross-section having a diameter that is substantially parallel to the first legs, the cross-section gradually changes to substantially oval in a second part of the length of the second legs, adjacent to the first part, the oval cross-section having a major axis that is substantially parallel to the first legs, and the cross-section remains substantially oval in a third part, adjacent to the second part, and in a fourth part, adjacent to the third part, of the length of the second legs, the oval cross-section having a major axis that progressively changes from substantially parallel to the first legs to substantially perpendicular to the first legs over the third part, and remains substantially perpendicular to the first legs in the fourth part to provide an effective thickness in the first leg direction that decreases in the second leg direction from a maximum adjacent the first legs; and (b) lifting force applying means for applying the lifting force to the first legs in a direction substantially parallel to the first leg direction.

8. The apparatus of claim 7, wherein the cross-section of the first part of the length of the second leg of the one of the angle-shaped elements is a mirror image of the cross-section of the first part of the length of the second leg of the other of the angle-shaped elements.

9. The apparatus of claim 7, wherein the major axis of the oval cross-section of the second legs of one of the angle-shaped elements changes from substantially parallel to the first legs to substantially perpendicular to the first legs in a first direction, and the major axis of the oval cross-section of the second legs of the other of the angle-shaped elements changes from substantially parallel to the first legs to substantially perpendicular to the first legs in the first direction.

10. The apparatus of claim 7, wherein the second legs of the angle-shaped elements have a closed position wherein the second legs are substantially parallel to one another, the first and second parts of the length of the second leg of one of the angle-shaped elements being substantially parallel to the first and second parts of the length of the second leg of the other of the angle-shaped elements in a first plane, and the fourth part of the length of the second leg of the one of the angle-shaped element being substantially parallel to the fourth part of the length of the second leg of the other of the angle-shaped elements in a plane substantially perpendicular to the first plane.

11. The apparatus of claim 7, wherein the first part, the second part, the third part, and the fourth part of the lengths of the second legs each have a length approximately equal to one-fourth of the length of the second legs.

12. Apparatus for atraumatically and properitoneally lifting an abdominal wall by applying a lifting force of greater than ten kilograms thereto, the abdominal wall including a properitoneal fat layer and a peritoneum, the apparatus comprising:

(a) a pair of angle-shaped elements moveable relative to one another, the angle-shaped elements including:
  (1) first legs disposed in a generally parallel relationship, the first legs having a first leg direction, and
  (2) elongate second legs extending from the first legs towards distal ends in a second leg direction, substantially perpendicular to the first leg direction, the second legs:
    (i) fanning out upon rotation of the first legs relative to one another,
    (ii) being shaped to include a broad lifting surface substantially perpendicular to the first leg direction,
    (iii) being adapted for separating the peritoneum from the properitoneal fat layer by inserting therebetween to engage the lifting surface with the properitoneal fat layer,
    (iv) having a stiffness in the first leg direction that decreases in the second leg direction from a maximum adjacent the first legs, and
    (v) having a width perpendicular to the first leg direction that increases in the second leg direction to a maximum adjacent the distal ends and to the second leg direction, and a thickness in the first leg direction, the width being plural times the thickness adjacent the distal ends; and (b) lifting force applying means for applying the lifting force to the first legs in a direction substantially parallel to the first leg direction.

13. Apparatus for lifting an abdominal wall by applying a lifting force thereto, the abdominal wall including a properitoneal fat layer and a peritoneum, the apparatus comprising:

(a) a pair of angle-shaped elements moveable relative to one another, the angle-shaped elements including:
  (1) first legs disposed in a generally parallel relationship, the first legs having a first leg direction,
  (2) elongate second legs extending from the first legs in a second leg direction, substantially perpendicular to the first leg direction, the second legs:
    (i) fanning out upon rotation of the first legs relative to one another;
    (ii) each having a length and a cross-section, wherein:
      the cross-section is substantially semicircular in a first part of the length of the second legs, proximal to the first legs, the semi-circular cross-section having a diameter that is substantially parallel to the first legs,
      the cross-section gradually changes to substantially oblong in a second part of the length of the second legs, adjacent to the first part, the oblong cross-section having a long axis that is substantially parallel to the first legs, and
      the cross-section remains substantially oblong in a third part, adjacent to the second part, and in a fourth part, adjacent to the third part, of the length of the second legs, the oblong cross-section having a long axis that progressively changes from substantially parallel to the first legs to substantially perpendicular to the first legs over the third part, and remains substantially perpendicular to the first legs in the fourth part to provide stiffness in the first leg direction that decreases in the second leg direction from a maximum adjacent the first legs; and (b) lifting force applying means for applying the lifting force to the first legs in a direction substantially parallel to the first leg direction.

14. The apparatus of claim 13, wherein the cross-section of the first part of the length of the second leg of one of the angle-shaped elements is a mirror image of the cross-section of the first part of the length of the second leg of the other of the angle-shaped elements.

15. The apparatus of claim 13, wherein the long axis of the oblong cross-section of the second legs of one of the angle-shaped elements changes from substantially parallel to the first legs to substantially perpendicular to the first legs in a first direction, and the long axis of the oblong cross-section of the second leg of the other of the angle-shaped elements changes from substantially parallel to the first legs to substantially perpendicular to the first legs in the first direction.

16. The apparatus of claim 13, wherein the second legs of the angle-shaped elements have a closed position wherein the second legs are substantially parallel to one another, the first and second parts of the length of the second leg of one of the angle-shaped elements being substantially parallel to the first and second parts of the length of the second leg of the other of the angle-shaped elements in a first plane, and the fourth part of the length of the second leg of one of the angle-shaped elements being substantially parallel to the fourth part of the length of the second leg of the other of the angle-shaped elements in a plane substantially perpendicular to the first plane.

17. The apparatus of claim 13, wherein the first part, the second part, the third part, and the fourth part of the lengths of the second legs each have a length approximately equal to one-fourth of the length of the second legs.

18. Apparatus for lifting an abdominal wall by applying a lifting force thereto, the abdominal wall including a properitoneal fat layer and a peritoneum, the apparatus comprising:

(a) a pair of angle-shaped elements moveable relative to one another, the angle-shaped elements including:
  (1) first legs disposed in a generally parallel relationship, the first legs having a first leg direction,
  (2) elongate second legs extending from the first legs in a second leg direction, substantially perpendicular to the first leg direction, the second legs:
    (i) fanning out upon rotation of the first legs relative to one another;
    (ii) each having a length and a cross-section, wherein:
      the cross-section is substantially semi-circular in a first part of the length of the second legs, proximal to the first legs, the semi-circular cross-section having a diameter that is substantially parallel to the first legs, the cross-section gradually changes to substantially oval in a second part of the length of the second legs, adjacent to the first part, the oval cross-section having a major axis that is substantially parallel to the first legs, and the cross-section remains substantially oval in a third part, adjacent to the second part, and in a fourth part, adjacent to the third part, of the length of the second legs, the oval cross-section having a major axis that progressively changes from substantially parallel to the first legs to substantially perpendicular to the first legs over the third part, and remains substantially perpendicular to the first legs in the fourth part to provide stiffness in the first leg direction that decreases in the second leg direction from a maximum adjacent the first legs; and (b) lifting force applying means for applying the lifting force to the firs legs in a direction substantially parallel to the first leg direction.

19. The apparatus of claim 18, wherein the cross-section of the first part of the length of the second leg of one of the angle-shaped elements is a mirror image of the cross-section of the first part of the length of the second leg of the other of the angle-shaped elements.

20. The apparatus of claim 18, wherein the major axis of the oval cross-section of the second legs of one of the angle-shaped elements changes from substantially parallel to the first legs to substantially perpendicular to the first legs in a first direction, and the major axis of the oval cross-section of the second leg of the other of the angle-shaped elements changes from substantially parallel to the first legs to substantially perpendicular to the first legs in the first direction.

21. The apparatus of claim 18, wherein the second legs of the angle-shaped elements have a closed position wherein the second legs are substantially parallel to one another, the first and second parts of the length of the second leg of one of the angle-shaped elements being substantially parallel to the first and second parts of the length of the second leg of the other of the angle-shaped elements in a first plane, and the fourth part of the length of the second leg of one of the angle-shaped elements being substantially parallel to the fourth part of the length of the second leg of the other of the angle-shaped elements in a plane substantially perpendicular to the first plane.

22. The apparatus of claim 18, wherein the first part, the second part, the third part, and the fourth part of the lengths of the second legs each have a length approximately equal to one-fourth of the length of the second legs.

23. Apparatus for lifting the abdominal wall, the apparatus comprising:

(a) a pair of angle-shaped elements moveable relative to one another, the angle-shaped elements including:

(1) first legs disposed in a generally parallel relationship, and (2) second legs extending laterally from the first legs, the second legs fanning out upon rotation of the first legs relative to one another, and being adapted for engagement with the abdominal wall;

(b) a contrarotating means, responsive to rotation of one of the angle-shaped elements through a first angle, for rotating the other of the first angle-shaped elements through an angle substantially equal and opposite to the first angle; and (c) lifting means for applying a lifting force to the angle-shaped elements.

24. The apparatus of claim 23, wherein the contrarotating means comprises a peg extending radially from the first leg of the one of the angle-shaped elements engaging in a socket radially disposed in the first leg of the other of the angle-shaped elements.

25. The apparatus of claim 23, wherein the contrarotating means comprises a gear on the first leg of one of the angle-shaped elements meshing with a gear on the first leg of the other of the angle-shaped elements.

26. The apparatus of claim 23, wherein the contrarotating means comprises part of the first leg of one of the angle-shaped elements in frictional contact with part of the first leg of the other of the angle-shaped elements.

27. The apparatus of claim 23, additionally comprising an operating means, attached to the angle-shaped elements, for rotating the angle-shaped elements with respect to one another.

28. The apparatus of claim 27, wherein the operating means comprises a lever attached to the first leg of each angle-shaped element distal from the second leg, each lever being substantially parallel to the second legs in first plane, and being angularly offset from the second legs in a plane perpendicular to the first plane.

29. The apparatus of claim 28, wherein the second legs of the angle-shaped elements have a closed position wherein the second legs are substantially parallel to one another, and an open position, and the second legs are moved from the closed position to the open position by squeezing the levers together.

30. The apparatus of claim 27, wherein the second legs of the angle-shaped elements have a closed position wherein the second legs are substantially parallel to one another, and an open position, and the operating means additionally comprises a locking means, coupled to the operating means, for locking the second legs in the closed position, and for locking the second legs in the open position.

31. The apparatus of claim 23, wherein:

the first legs have a direction, and the second legs have a stiffness in the direction of the first legs that decreases distally from the first legs.

32. The apparatus of claim 23, wherein:

the first legs have a direction, and the second legs have an effective thickness in the direction of the first legs that decreases distally from the first legs.

33. Apparatus for atraumatically and properitoneally lifting the abdominal wall by applying a lifting force of greater than ten kilograms thereto, the apparatus comprising:

(a) a pair of angle-shaped elements moveable relative to one another, the angle-shaped elements including:

(1) first legs disposed in a generally parallel relationship, the first legs having a first leg direction, and (2) elongate second legs extending from the first legs towards distal ends in a second leg direction, substantially perpendicular to the first leg direction, the second legs fanning out upon rotation of the first legs relative to one another, being shaped to include a broad lifting surface substantially perpendicular to the first leg direction, being adapted for insertion through the abdominal wall to engage the broad lifting surface with the abdominal wall, and having a width perpendicular to the first leg direction that increases in the second leg direction to a maximum adjacent the distal ends, and to the second leg direction and a thickness in the first leg direction, the width being plural times the thickness adjacent the distal ends;

(b) lifting force applying means for compliantly applying the lifting force to the first legs in a direction substantially parallel to the first leg direction; and (c) force measuring means, coupled between the lifting force applying means and the first legs, for measuring the lifting force applied to the abdominal wall.

34. The apparatus of claim 33, wherein the second legs have a stiffness in the first leg direction that decreases in the second leg direction from a maximum adjacent the first legs.

35. The apparatus of claim 33, wherein the second legs have an effective thickness in the first leg direction that decreases in the second leg direction from a maximum adjacent the first legs.

36. Apparatus for lifting the abdominal wall by applying a lifting force thereto, the apparatus comprising:

(a) a pair of angle-shaped elements moveable relative to one another, the angle-shaped elements including:
  (1) first legs disposed in a generally parallel relationship, the first legs having a first leg direction, and
  (2) elongate second legs extending from the first legs in a second leg direction, substantially perpendicular to the first leg direction, the second legs fanning out upon rotation of the first legs relative to one another, being shaped to include a broad lifting surface substantially perpendicular to the first leg direction, and being adapted for insertion through the abdominal wall to engage the broad lifting surface with the abdominal wall;

(b) lifting force applying means for compliantly applying the lifting force to the first legs in a direction substantially parallel to the first leg direction, the lifting force applying means comprising:
  (1) a cylindrical sleeve having a bore with a lip partway along, the bore receiving the first legs of the angle-shaped members, and
  (2) means for attaching the cylindrical sleeve to a lifting arm; and (c) force measuring means, coupled between the lifting force applying means and the first legs, for measuring the lifting force applied to the abdominal wall, the force measuring means comprising:
  (1) a mounting block, slidably mounted in the bore of the cylindrical sleeve, the mounting block being cylindrical, and including a contact face, and a force indicating means for indicating the lifting force, the first legs of the angle-shaped elements being rotatably mounted in the mounting block with the second legs facing the contact face, and
  (2) a coil spring, disposed within the bore of the cylindrical sleeve between the lip and the contact face of the mounting block, and surrounding the first legs of the angle-shaped elements.

37. The apparatus of claim 36, wherein the lifting force applying means additionally comprises a dovetail attached to the cylindrical sleeve.

38. The apparatus of claim 36, wherein:
the mounting block has an axial movement relative to the cylindrical sleeve in response to the lifting force, and
the force indicating means indicates the lifting force in response to the axial movement of the mounting block.

39. The apparatus of claim 38, wherein:
the mounting block additionally includes a surface adjacent the cylindrical sleeve, and
the force indicating means comprises a scale marked on the surface adjacent to the cylindrical sleeve.

40. The apparatus of claim 38, wherein:
(a) the mounting block additionally includes:
  (1) a second face opposite the contact face, the second face including a window having a reference mark, and
  (2) a curved groove adjacent to the window, and
(b) the force indicating means additionally comprises an elongate tape, including:
  (1) an end attached to the bore of the cylindrical sleeve,
  (2) a face marked with a scale, and
  (3) an edge engaging in the curved groove such that the scale appears in the window adjacent to the reference mark.

41. The apparatus of claim 38, wherein:
(a) the mounting block additionally includes:
  (1) a second face opposite the contact face, the second face including a window marked with a scale, and
  (2) a curved groove adjacent to the window, and
(b) the indicating means additionally comprises an elongate tape, including:
  (1) an end attached to the bore of the cylindrical sleeve,
  (2) a face marked with a reference mark, and
  (3) an edge engaging in the curved groove such that the reference mark appears in the window adjacent to the scale.

42. Apparatus for lifting the abdominal wall by applying a lifting force thereto, the lifting force being in a lifting direction to lift the abdominal wall, the apparatus comprising:

(a) a pair of angle-shaped elements moveable relative to one another, the angle-shaped elements including:
  (1) first legs disposed in a generally parallel relationship, the first legs having a first leg direction, and
  (2) elongate second legs extending from the first legs in a second leg direction, substantially perpendicular to the first leg direction, the second legs fanning out upon rotation of the first legs relative to one another, being shaped to include a broad lifting surface substantially perpendicular to the first leg direction, and being adapted for insertion through the abdominal wall to engage the broad lifting surface with the abdominal wall, the second legs effectively applying the lifting force to the abdominal wall at an offset from the first legs;

(b) lifting force applying means for applying the lifting force to the first legs in the lifting direction, substantially parallel to the first leg direction, and for applying torque to the first legs to counter torque resulting from the offset, the lifting force applying means including unidirectional coupling means for transmitting an external force and an external torque to the lifting force applying means to provide the lifting force and the torque, the unidirectional coupling means transmitting the external force and the external torque only when the lifting force applied to the abdominal wall is in the lifting direction.

43. The apparatus of claim 42, wherein the unidirectional coupling means comprises a dovetail connector.

44. A method of lifting an abdominal wall by applying a lifting force thereto, the abdominal wall including a properitoneal fat layer and a peritoneum, the method comprising the steps of:

(a) providing a retractor including an angle-shaped element having:
   (1) a first leg having a first leg direction, and
   (2) a second leg extending from the first leg towards a distal end, the second leg extending in a second leg direction substantially perpendicular to the first leg direction, and being shaped to include a broad lifting surface substantially perpendicular to the first leg direction;
(b) making an incision through the abdominal wall except the peritoneum;
(c) inserting the distal end of the second leg into the incision to abut the peritoneum;
(d) advancing the second leg between the properitoneal fat layer and the peritoneum to engage the broad lifting surface with the properitoneal fat layer; and
(e) applying the lifting force to the first leg in a direction substantially parallel to the first leg direction.

45. The method of claim 44, wherein
the step of providing a retractor provides a retractor including a second leg having a stiffness in the first leg direction that decreases in the second leg direction from a maximum adjacent the first leg.

46. The method of claim 44, wherein
the step of providing a retractor provides a retractor including a second leg having an effective thickness in the first leg direction that decreases in the second leg direction from a maximum adjacent the first leg.

47. A method of properitoneally lifting an abdominal wall by applying a lifting force thereto, the abdominal wall including a properitoneal fat layer and a peritoneum, the method comprising steps of:
(a) providing a retractor including a pair of angle-shaped elements moveable relative to one another and including:
   (1) first legs disposed in a generally parallel relationship, the first legs having a first leg direction, and
   (2) elongate second legs extending from the first legs towards distal ends, the second legs extending in a second leg direction, substantially perpendicular to the first leg direction, the second legs fanning out from a closed state upon rotation of the first legs relative to one another, and being shaped to include a broad lifting surface substantially perpendicular to the first leg direction;
(b) making an incision through the abdominal wall except for the peritoneum;
(c) inserting the distal ends of the second legs in the closed state into the incision to abut the peritoneum;
(d) advancing the second legs in the closed state between the properitoneal fat layer and the peritoneum to engage the broad lifting surface with the properitoneal fat layer;
(e) rotating the first legs relative to one another to fan out the second legs; and
(f) applying the lifting force to the first legs in a direction substantially parallel to the first leg direction.

48. The method of claim 47, wherein
the step of providing a retractor provides a retractor including second legs having a stiffness in the first leg direction that decreases in the second leg direction from a maximum adjacent the first legs.

49. The method of claim 47, wherein
the step of providing a retractor provides a retractor including second legs having an effective thickness in the first leg direction that decreases in the second leg direction from a maximum adjacent the first legs.

50. The method of claim 47, wherein:
the step of advancing the the second legs between the properitoneal fat layer and the peritoneum detaches a part of the peritoneum from the peritoneal fat layer, and
the step of rotating the first legs relative to one another to fan out the second legs detaches a further part of the peritoneum from the peritoneal fat layer.

51. The method of claim 47, wherein:
the step of providing a retractor provides a retractor additionally including a lifting force indicator, and
the step of applying the lifting force to the first legs includes a step of observing the lifting force indicator to determine the lifting force.

52. A method of lifting an abdominal wall by applying a lifting force thereto, the abdominal wall including a peritoneum, the method comprising steps of:
(a) providing a retractor including a pair of angle-shaped elements moveable relative to one another, and including:
   (1) first legs disposed in a generally parallel relationship, the first legs having a first leg direction, and
   (2) elongate second legs extending from the first legs towards distal ends in a second leg direction, substantially perpendicular to the first leg direction, the second legs:
      (i) fanning out from a closed state upon rotation of the first legs relative to one another,
      (ii) being shaped to include a broad lifting surface substantially perpendicular to the first leg direction, and
      (iii) having a stiffness in the first leg direction that decreases in the second leg direction from a maximum adjacent the first legs;
(b) making an incision through the abdominal wall;
(c) inserting the second legs in the closed state through the incision;
(d) rotating the first legs relative to one another to fan out the second legs;
(e) engaging the broad lifting surface of the second legs with the peritoneum; and
(f) applying the lifting force to the first legs in a direction substantially parallel to the first leg direction.

53. A method of lifting an abdominal wall by applying a lifting force thereto, the method comprising steps of:
(a) providing a retractor including a pair of angle-shaped elements moveable relative to one another, and including:
   (1) first legs disposed in a generally parallel relationship, the first legs having a first leg direction and being linked together such that rotation of one of the first legs through a first angle rotates tile other of the first legs through an angle equal and opposite to the first angle, and
   (2) elongate second legs extending from the first legs in a second leg direction, substantially perpendicular to the first leg direction, the second legs fanning out symmetrically from a closed state upon equal and opposite rotation of the first legs relative to one another;
(b) making an incision through the abdominal wall;
(c) inserting the second legs through the incision;
(d) rotating the first legs relative to one another to symmetrically fan out the second legs from the closed state;

(e) engaging the second legs with the abdominal wall; and (f) applying the lifting force to the angle-shaped elements.

54. A method of lifting an abdominal wall by applying a lifting force thereto, the method comprising steps of:
- (a) providing a retractor including a pair of angle-shaped elements moveable relative to one another, and including:
  - (1) first legs disposed in a generally parallel relationship, the first legs having a first leg direction
  - (2) elongate, second legs extending from the first legs in a second leg direction, substantially perpendicular to the first leg direction, the second legs fanning out from a closed state upon rotation of the first legs relative to one another, and being shaped to include a broad lifting surface substantially perpendicular to the first leg direction, and
  - (3) force measuring means for measuring the lifting force;
- (b) making an incision through the abdominal wall;
- (c) inserting the second legs in the closed state into the incision;
- (d) rotating the first legs relative to one another to fan out the second legs;
- (e) engaging the broad lifting surface of the second legs with the abdominal wall;
- (f) applying the lifting force to the first legs in a direction substantially parallel to the first leg direction; and
- (g) during the step of applying the lifting force, observing the lifting force using the force measuring means.

* * * * *